US010314736B2

(12) United States Patent
Catalano

(10) Patent No.: US 10,314,736 B2
(45) Date of Patent: Jun. 11, 2019

(54) METHOD AND APPARATUS FOR TREATING OBSTRUCTIVE SLEEP APNEA (OSA)

(71) Applicant: Peter J. Catalano, North Andover, MA (US)

(72) Inventor: Peter J. Catalano, North Andover, MA (US)

(73) Assignee: Cook Medical Technologies LLC, Bloomington, IN (US)

( * ) Notice: Subject to any disclaimer, the term of this patent is extended or adjusted under 35 U.S.C. 154(b) by 206 days.

(21) Appl. No.: 14/055,159

(22) Filed: Oct. 16, 2013

(65) Prior Publication Data
US 2014/0102460 A1    Apr. 17, 2014

Related U.S. Application Data

(60) Provisional application No. 61/714,596, filed on Oct. 16, 2012.

(51) Int. Cl.
*A61F 5/56* (2006.01)
(52) U.S. Cl.
CPC .................................... *A61F 5/566* (2013.01)
(58) Field of Classification Search
CPC ........... A61F 2/0811; A61F 2/08–2/105; A61F 2/0063; A61F 2002/0068–2002/0072; A61F 2002/0817–2002/0894; A61F 5/56–5/566; A61B 17/0057; A61B 2017/00575–2017/00676;
(Continued)

(56) References Cited

U.S. PATENT DOCUMENTS

| 4,024,859 A | 5/1977 | Slepyan et al. |
| 4,064,873 A | 12/1977 | Swenson |

(Continued)

FOREIGN PATENT DOCUMENTS

| WO | WO2007056583 | 5/2007 |
| WO | 2007146338 A2 | 12/2007 |

(Continued)

OTHER PUBLICATIONS

International Searching Authority, International Search Report and Written Opinion for International application No. PCT/US2014/049341, dated Nov. 19, 2014, pp. 1-11.

(Continued)

*Primary Examiner* — Victoria J Hicks
*Assistant Examiner* — Michelle J Lee
(74) *Attorney, Agent, or Firm* — Buchanan Van Tuinen LLC

(57) ABSTRACT

A method for treating obstructive sleep apnea is described herein. The method includes the step of providing a tethering device having an elastic filament having a distal end and a proximal end and a flexible memory head mounted to the distal end of the elastic filament. The method further includes the steps of advancing the tethering device through the tongue of a patient so that the flexible memory head of the tethering device is disposed against the back of the tongue and the elastic filament of the tethering device extends through the tongue and securing the proximal end of the elastic filament to the mandible of the patient under tension, whereby to restrain rearward movement of the tongue while the patient is sleeping.

19 Claims, 36 Drawing Sheets

(58) Field of Classification Search
CPC .......................... A61B 17/04–17/0401; A61B 2017/0403–2017/048
USPC .......................................... 128/848; 606/191
See application file for complete search history.

(56) References Cited

U.S. PATENT DOCUMENTS

| | | | |
|---|---|---|---|
| 4,608,972 A | 9/1986 | Small | |
| 4,917,604 A | 4/1990 | Small | |
| 5,308,318 A | 5/1994 | Plassche, Jr. | |
| 5,460,182 A * | 10/1995 | Goodman | A61B 5/0084 600/342 |
| 5,477,860 A | 12/1995 | Essen-Moller | |
| 5,489,278 A | 2/1996 | Abrahamson | |
| 5,674,191 A | 10/1997 | Edwards et al. | |
| 5,715,840 A | 2/1998 | Hall | |
| 5,954,050 A | 9/1999 | Christopher | |
| 5,974,724 A | 9/1999 | Frantz et al. | |
| 5,988,171 A | 11/1999 | Sohn et al. | |
| 6,159,158 A | 12/2000 | Lowe | |
| 6,159,208 A | 12/2000 | Hovda et al. | |
| 6,161,541 A | 12/2000 | Woodson | |
| 6,397,841 B1 | 6/2002 | Kenyon et al. | |
| 6,408,851 B1 | 6/2002 | Karell | |
| 6,505,625 B1 | 1/2003 | Uenishi | |
| 6,513,530 B2 | 2/2003 | Knudson et al. | |
| 6,513,531 B2 | 2/2003 | Knudson et al. | |
| 6,523,541 B2 | 2/2003 | Knudson et al. | |
| 6,527,737 B2 | 3/2003 | Kaneshige | |
| 6,536,424 B2 | 3/2003 | Fitton | |
| 6,536,439 B1 | 3/2003 | Palmisano | |
| 6,619,290 B1 | 9/2003 | Zacco | |
| 6,895,963 B1 | 5/2005 | Martin et al. | |
| 6,910,483 B2 | 6/2005 | Daly et al. | |
| 6,955,172 B2 | 10/2005 | Nelson et al. | |
| 6,966,319 B2 | 11/2005 | Fitton | |
| 6,974,419 B1 | 12/2005 | Voss et al. | |
| 7,004,172 B1 | 2/2006 | Zacco | |
| 7,004,941 B2 | 2/2006 | Tvinnereim et al. | |
| 7,037,290 B2 | 5/2006 | Gardeski et al. | |
| 7,047,979 B2 | 5/2006 | Conrad et al. | |
| 7,063,089 B2 | 6/2006 | Knudson et al. | |
| 7,073,505 B2 | 7/2006 | Nelson et al. | |
| 7,090,672 B2 | 8/2006 | Underwood et al. | |
| 7,128,069 B2 | 10/2006 | Farrugia et al. | |
| 7,168,429 B2 | 1/2007 | Matthews et al. | |
| 7,188,627 B2 | 3/2007 | Nelson et al. | |
| 7,213,599 B2 | 5/2007 | Conrad et al. | |
| 7,216,647 B2 | 5/2007 | Lang et al. | |
| 7,232,462 B2 | 6/2007 | Schaeffer | |
| 7,237,554 B2 | 7/2007 | Conrad et al. | |
| 7,255,109 B2 | 8/2007 | Knudson et al. | |
| 7,269,453 B2 | 9/2007 | Mogul | |
| 7,291,112 B2 | 11/2007 | Martin et al. | |
| 7,337,778 B2 | 3/2008 | Martin et al. | |
| 7,337,781 B2 | 3/2008 | Vassallo | |
| 7,360,542 B2 | 4/2008 | Nelson et al. | |
| 7,363,926 B2 | 4/2008 | Pflueger et al. | |
| 7,387,634 B2 | 6/2008 | Benderev | |
| 7,401,611 B2 | 7/2008 | Conrad et al. | |
| 7,491,200 B2 | 2/2009 | Underwood | |
| 7,607,439 B2 | 10/2009 | Li | |
| 7,644,714 B2 | 1/2010 | Atkinson et al. | |
| 7,658,192 B2 | 2/2010 | Harrington | |
| 7,669,603 B2 | 3/2010 | Knudson et al. | |
| 7,673,635 B2 | 3/2010 | Conrad et al. | |
| 7,680,538 B2 | 3/2010 | Durand et al. | |
| 7,703,460 B2 | 4/2010 | Conrad et al. | |
| 7,766,926 B2 | 8/2010 | Bosley, Jr. et al. | |
| 7,770,582 B2 | 8/2010 | Chen et al. | |
| 7,789,843 B2 | 9/2010 | Ray | |
| 7,793,661 B2 | 9/2010 | Macken | |
| 7,798,149 B2 | 9/2010 | Haduong | |
| 7,810,502 B1 | 10/2010 | Nguyen et al. | |
| 7,810,503 B2 | 10/2010 | Magnin | |
| 7,813,812 B2 | 10/2010 | Kieval et al. | |
| 7,819,122 B2 | 10/2010 | Abramson | |
| 7,827,038 B2 | 11/2010 | Richard et al. | |
| 7,827,988 B2 | 11/2010 | Matthews et al. | |
| 7,827,991 B2 | 11/2010 | Maher | |
| 7,832,402 B2 | 11/2010 | Nelissen | |
| 7,832,403 B2 | 11/2010 | Halstrom et al. | |
| 7,836,888 B2 | 11/2010 | Hegde et al. | |
| 7,836,889 B2 | 11/2010 | Kusukawa | |
| 7,845,356 B2 | 12/2010 | Paraschac et al. | |
| 7,845,357 B2 | 12/2010 | Buscemi et al. | |
| 7,856,979 B2 | 12/2010 | Doshi et al. | |
| 7,856,980 B2 | 12/2010 | Lang et al. | |
| 7,861,722 B2 | 1/2011 | Keropian | |
| 7,861,723 B2 | 1/2011 | Dedrick et al. | |
| 7,861,724 B2 | 1/2011 | Keropian | |
| 7,862,721 B2 | 1/2011 | Bergersen | |
| 7,870,860 B2 | 1/2011 | McCormick et al. | |
| 7,874,291 B2 | 1/2011 | Ging et al. | |
| 7,874,294 B2 | 1/2011 | Burger | |
| 7,884,101 B2 | 2/2011 | Teegarden et al. | |
| 7,909,037 B2 | 3/2011 | Hegde et al. | |
| 7,909,038 B2 | 3/2011 | Hegde et al. | |
| 7,918,228 B2 | 4/2011 | Smernoff | |
| 7,921,850 B2 | 4/2011 | Nelson et al. | |
| 7,934,506 B2 | 5/2011 | Woodson et al. | |
| 7,935,065 B2 | 5/2011 | Martin et al. | |
| 7,938,114 B2 | 5/2011 | Matthews et al. | |
| 7,949,400 B2 | 5/2011 | Kieval et al. | |
| 7,954,494 B1 | 6/2011 | Connor | |
| 7,954,496 B2 | 6/2011 | Jansheski et al. | |
| 7,955,267 B2 | 6/2011 | Voss et al. | |
| 7,958,895 B2 | 6/2011 | Nelson et al. | |
| 7,958,896 B2 | 6/2011 | Nelson et al. | |
| 7,959,554 B2 | 6/2011 | McAlexander et al. | |
| 7,971,591 B2 | 7/2011 | Jansheski | |
| 7,975,700 B2 | 7/2011 | Frazier et al. | |
| 7,975,701 B2 | 7/2011 | Bergersen | |
| 7,976,471 B2 | 7/2011 | Martin et al. | |
| 7,980,248 B2 | 7/2011 | Hegde et al. | |
| 7,984,714 B2 | 7/2011 | Hausmann et al. | |
| 7,987,854 B2 | 8/2011 | Arni | |
| 7,992,564 B2 | 8/2011 | Doshi et al. | |
| 7,992,566 B2 | 8/2011 | Pflueger et al. | |
| 7,992,567 B2 | 8/2011 | Hirotsuka et al. | |
| 7,997,266 B2 | 8/2011 | Frazier et al. | |
| 7,997,267 B2 | 8/2011 | Ging et al. | |
| 7,997,276 B2 | 8/2011 | Goff | |
| 8,001,971 B2 | 8/2011 | Boucher et al. | |
| 8,001,972 B2 | 8/2011 | Eubank | |
| 8,001,973 B2 | 8/2011 | Sotos et al. | |
| 8,015,975 B2 | 9/2011 | Zohlmann, Jr. | |
| 8,020,560 B2 | 9/2011 | Paraschac et al. | |
| 8,025,063 B2 | 9/2011 | Sotos et al. | |
| 8,026,405 B2 | 9/2011 | Beaudry | |
| 8,028,703 B1 | 10/2011 | Moses | |
| 8,033,282 B2 | 10/2011 | Eubank | |
| 8,037,885 B2 | 10/2011 | Metzger et al. | |
| 8,037,886 B2 | 10/2011 | Sotos et al. | |
| 8,047,201 B2 | 11/2011 | Guyuron et al. | |
| 8,047,206 B2 | 11/2011 | Boucher et al. | |
| 8,070,693 B2 | 12/2011 | Ayala et al. | |
| 8,074,655 B2 | 12/2011 | Sanders | |
| 8,096,303 B2 | 1/2012 | Dineen et al. | |
| 8,167,787 B2 | 5/2012 | Gillis | |
| 8,186,355 B2 | 5/2012 | Van Der Burg et al. | |
| 8,220,466 B2 | 7/2012 | Frazier et al. | |
| 8,220,467 B2 | 7/2012 | Sanders | |
| 8,327,854 B2 | 12/2012 | Gillis et al. | |
| 8,425,466 B2 | 4/2013 | Sargent, Jr. | |
| 8,460,322 B2 | 6/2013 | van der Burg et al. | |
| 8,535,310 B2 | 9/2013 | Hardin, Jr. et al. | |
| 8,535,349 B2 | 9/2013 | Chen et al. | |
| 8,603,185 B2 | 12/2013 | Shah et al. | |
| 2001/0050085 A1 | 12/2001 | Knudson et al. | |
| 2002/0198562 A1* | 12/2002 | Akerfeldt et al. | A61B 17/08 606/213 |
| 2003/0111079 A1 | 6/2003 | Matthews et al. | |
| 2003/0140925 A1 | 7/2003 | Sapienza et al. | |

(56) References Cited

U.S. PATENT DOCUMENTS

| | | |
|---|---|---|
| 2003/0168064 A1 | 9/2003 | Daly et al. |
| 2004/0028676 A1 | 2/2004 | Klein et al. |
| 2004/0073272 A1 | 4/2004 | Knudson et al. |
| 2004/0099275 A1 | 5/2004 | Zacco |
| 2004/0112387 A1 | 6/2004 | Lang et al. |
| 2004/0153127 A1 | 8/2004 | Gordon et al. |
| 2004/0187870 A1 | 9/2004 | Matthews et al. |
| 2005/0005937 A1 | 1/2005 | Farrugia et al. |
| 2005/0098184 A1 | 5/2005 | Conrad et al. |
| 2005/0103339 A1 | 5/2005 | Daly et al. |
| 2005/0126563 A1 | 6/2005 | van der Burg et al. |
| 2005/0217673 A1 | 10/2005 | Daly et al. |
| 2005/0256452 A1 | 11/2005 | DeMarchi et al. |
| 2005/0267547 A1 | 12/2005 | Knudson et al. |
| 2005/0268914 A1 | 12/2005 | Paoluccio et al. |
| 2005/0279365 A1 | 12/2005 | Armijo et al. |
| 2006/0000475 A1 | 1/2006 | Matthews et al. |
| 2006/0070626 A1 | 4/2006 | Frazier et al. |
| 2006/0112962 A1 | 6/2006 | Tebbutt et al. |
| 2006/0150986 A1 | 7/2006 | Roue et al. |
| 2006/0169289 A1 | 8/2006 | Zacco |
| 2006/0201519 A1 | 9/2006 | Frazier et al. |
| 2006/0201520 A1 | 9/2006 | Christensen, III |
| 2006/0207606 A1 | 9/2006 | Roue et al. |
| 2006/0207607 A1 | 9/2006 | Hirotsuka et al. |
| 2006/0207608 A1 | 9/2006 | Hirotsuka et al. |
| 2006/0207612 A1 | 9/2006 | Jackson et al. |
| 2006/0235264 A1 | 10/2006 | Vassallo |
| 2006/0235877 A1 | 10/2006 | Richard et al. |
| 2007/0132117 A1 | 6/2007 | Truitt et al. |
| 2007/0134085 A1 | 6/2007 | Daly et al. |
| 2007/0144539 A1 | 6/2007 | van der Burg et al. |
| 2007/0157928 A1 | 7/2007 | Pujol et al. |
| 2007/0157934 A1 | 7/2007 | Lang et al. |
| 2007/0207994 A1 | 9/2007 | Teegarden et al. |
| 2007/0209664 A1 | 9/2007 | Paraschac et al. |
| 2007/0209665 A1 | 9/2007 | Gillis et al. |
| 2007/0244086 A1 | 10/2007 | Teegarden et al. |
| 2007/0256693 A1 | 11/2007 | Paraschac et al. |
| 2007/0287923 A1 | 12/2007 | Adkins et al. |
| 2008/0023012 A1 | 1/2008 | Dineen et al. |
| 2008/0027480 A1 | 1/2008 | van der Burg et al. |
| 2008/0027560 A1 | 1/2008 | Jackson et al. |
| 2008/0035160 A1 | 2/2008 | Woodson et al. |
| 2008/0041382 A1 | 2/2008 | Matthews et al. |
| 2008/0041383 A1 | 2/2008 | Matthews et al. |
| 2008/0041398 A1 | 2/2008 | Hegde et al. |
| 2008/0045813 A1 | 2/2008 | Phuah et al. |
| 2008/0053461 A1 | 3/2008 | Hirotsuka et al. |
| 2008/0058584 A1 | 3/2008 | Hirotsuka et al. |
| 2008/0066753 A1 | 3/2008 | Martin et al. |
| 2008/0066765 A1 | 3/2008 | Paraschac et al. |
| 2008/0066767 A1 | 3/2008 | Paraschac et al. |
| 2008/0066769 A1 | 3/2008 | Dineen et al. |
| 2008/0078411 A1 | 4/2008 | Buscemi et al. |
| 2008/0097380 A1 | 4/2008 | Li |
| 2008/0099019 A1 | 5/2008 | Martin et al. |
| 2008/0115791 A1 | 5/2008 | Heine |
| 2008/0188947 A1* | 8/2008 | Sanders ............. A61B 17/0401 623/23.72 |
| 2008/0194953 A1 | 8/2008 | Kerber |
| 2008/0208264 A1 | 8/2008 | Frazier et al. |
| 2008/0208265 A1* | 8/2008 | Frazier ............... A61B 17/0401 606/326 |
| 2008/0251071 A1 | 10/2008 | Armitstead et al. |
| 2009/0044814 A1 | 2/2009 | Iancea et al. |
| 2009/0053306 A1 | 2/2009 | Agarwal et al. |
| 2009/0060905 A1 | 3/2009 | Martin et al. |
| 2009/0099471 A1 | 4/2009 | Broadley et al. |
| 2009/0131923 A1 | 5/2009 | Connors et al. |
| 2009/0177027 A1* | 7/2009 | Gillis .................... A61F 5/566 600/37 |
| 2009/0319046 A1 | 12/2009 | Krespi et al. |
| 2010/0004264 A1 | 1/2010 | Xiong et al. |
| 2010/0010061 A1 | 1/2010 | Cooper et al. |
| 2010/0016694 A1 | 1/2010 | Martin et al. |
| 2010/0024830 A1 | 2/2010 | Rousseau et al. |
| 2010/0028026 A1 | 2/2010 | Inami et al. |
| 2010/0030011 A1 | 2/2010 | Weadock et al. |
| 2010/0037901 A1 | 2/2010 | Rousseau et al. |
| 2010/0106246 A1 | 4/2010 | Rousseau et al. |
| 2010/0108066 A1 | 5/2010 | Martin et al. |
| 2010/0108077 A1 | 5/2010 | Lindh et al. |
| 2010/0132719 A1 | 6/2010 | Jacobs et al. |
| 2010/0137891 A1 | 6/2010 | Shalon et al. |
| 2010/0137905 A1 | 6/2010 | Weadock et al. |
| 2010/0144701 A1 | 6/2010 | Cooper et al. |
| 2010/0211184 A1 | 8/2010 | Rousseau et al. |
| 2010/0234946 A1 | 9/2010 | Rousseau |
| 2010/0286793 A1 | 11/2010 | Newman et al. |
| 2010/0300458 A1 | 12/2010 | Stubbs et al. |
| 2011/0005526 A1 | 1/2011 | Garabadian et al. |
| 2011/0005529 A1 | 1/2011 | Doshi et al. |
| 2011/0005530 A1 | 1/2011 | Doshi et al. |
| 2011/0017220 A1 | 1/2011 | Lindsay et al. |
| 2011/0030700 A1 | 2/2011 | Wilson |
| 2011/0030701 A1 | 2/2011 | Lang et al. |
| 2011/0036357 A1 | 2/2011 | Abramson |
| 2011/0048430 A1 | 3/2011 | Arnon |
| 2011/0048431 A1 | 3/2011 | Li |
| 2011/0056498 A1 | 3/2011 | Lang et al. |
| 2011/0067708 A1 | 3/2011 | Doshi et al. |
| 2011/0067709 A1 | 3/2011 | Doshi et al. |
| 2011/0073119 A1 | 3/2011 | Chen et al. |
| 2011/0088701 A1 | 4/2011 | Thornton |
| 2011/0094520 A1 | 4/2011 | Mikhailenok et al. |
| 2011/0100376 A1 | 5/2011 | Rousseau |
| 2011/0100378 A1 | 5/2011 | Rousseau |
| 2011/0108041 A1 | 5/2011 | Sather et al. |
| 2011/0114099 A1 | 5/2011 | Goldstein |
| 2011/0120476 A1 | 5/2011 | Keropian |
| 2011/0130249 A1 | 6/2011 | Mikhailenok et al. |
| 2011/0132378 A1 | 6/2011 | Levendowski et al. |
| 2011/0155142 A1 | 6/2011 | Boucher et al. |
| 2011/0155143 A1 | 6/2011 | Shantha |
| 2011/0155144 A1 | 6/2011 | Toussaint |
| 2011/0162658 A1 | 7/2011 | Fisher et al. |
| 2011/0166673 A1 | 7/2011 | Patel et al. |
| 2011/0168186 A1 | 7/2011 | Halstrom |
| 2011/0168187 A1 | 7/2011 | Nelissen |
| 2011/0168188 A1 | 7/2011 | Moore et al. |
| 2011/0174315 A1 | 7/2011 | Zhang et al. |
| 2011/0178439 A1 | 7/2011 | Irwin et al. |
| 2011/0180075 A1 | 7/2011 | Chen et al. |
| 2011/0180076 A1 | 7/2011 | Hegde et al. |
| 2011/0183928 A1 | 7/2011 | Thede et al. |
| 2011/0192404 A1 | 8/2011 | Chen |
| 2011/0203598 A1 | 8/2011 | Favet et al. |
| 2011/0214678 A1 | 9/2011 | Zhang et al. |
| 2011/0218451 A1 | 9/2011 | Lai et al. |
| 2011/0220123 A1 | 9/2011 | Robson |
| 2011/0220124 A1 | 9/2011 | Vaska et al. |
| 2011/0220125 A1 | 9/2011 | Van Dyke et al. |
| 2011/0226261 A1 | 9/2011 | Hernandez |
| 2011/0226262 A1 | 9/2011 | Gillis et al. |
| 2011/0226263 A1 | 9/2011 | Gillis et al. |
| 2011/0226264 A1 | 9/2011 | Friedman et al. |
| 2011/0230727 A1* | 9/2011 | Sanders ................ A61F 5/566 600/237 |
| 2011/0232651 A1 | 9/2011 | Diers |
| 2011/0232652 A1 | 9/2011 | Levendowski et al. |
| 2011/0240037 A1 | 10/2011 | Hegde et al. |
| 2011/0240038 A1 | 10/2011 | Doshi et al. |
| 2011/0245850 A1 | 10/2011 | van der Burg et al. |
| 2011/0259345 A1 | 10/2011 | Cullen |
| 2011/0259346 A1 | 10/2011 | Tsuiki et al. |
| 2011/0265801 A1 | 11/2011 | Cullen |
| 2011/0265802 A1 | 11/2011 | Ha |
| 2011/0308530 A1 | 12/2011 | Gillis et al. |
| 2012/0022634 A1* | 1/2012 | Kusleika ................ A61L 29/02 623/1.11 |
| 2012/0138069 A1 | 6/2012 | Gillis et al. |
| 2012/0162401 A1 | 6/2012 | Melder et al. |
| 2012/0265055 A1 | 10/2012 | Melsheimer et al. |

(56) References Cited

U.S. PATENT DOCUMENTS

| | | |
|---|---|---|
| 2013/0041314 A1 | 2/2013 | Dillon |
| 2013/0046138 A1 | 2/2013 | McLawhorn |
| 2013/0056009 A1 | 3/2013 | Mohan et al. |
| 2013/0085546 A1 | 4/2013 | Bolea et al. |
| 2013/0180528 A1 | 7/2013 | Zhou et al. |
| 2013/0213409 A1 | 8/2013 | Podmore et al. |
| 2013/0226146 A1 | 8/2013 | Tekulve |
| 2013/0238003 A1 | 9/2013 | Fischer et al. |

FOREIGN PATENT DOCUMENTS

| | | |
|---|---|---|
| WO | 2007146338 A3 | 12/2007 |
| WO | 2007149469 | 12/2007 |
| WO | 2009140197 | 11/2009 |
| WO | WO2010045546 | 4/2010 |
| WO | WO2010051195 | 5/2010 |
| WO | WO2011068952 | 6/2011 |
| WO | 2011091189 A1 | 7/2011 |
| WO | WO2011123714 | 10/2011 |
| WO | 2011151745 | 12/2011 |
| WO | 2011151745 A1 | 12/2011 |
| WO | WO2013010169 | 1/2013 |

OTHER PUBLICATIONS

File history of U.S. Appl. No. 08/883,220, now U.S. Pat. No. 5,988,171, as of Jun. 3, 2014. filed Jun. 26, 1997. First Named Inventor, Ze'ev Sohn. Title, Methods and Devices for the Treatment of Airway Obstruction, Sleep Apnea and Snoring.

File history of U.S. Appl. No. 10/877,003, now U.S. Pat. No. 7,213,599, as of Jun. 3, 2014. filed Jun. 24, 2004. First Named Inventor, Timothy R. Conrad. Title, Airway Implant.

File history of U.S. Appl. No. 11/757,501, now U.S. Pat. No. 7,703,460, as of Jun. 3, 2014. filed Jun. 4, 2007. First Named Inventor, Timothy R. Conrad. Title, Tongue Implant.

File history of U.S. Appl. No. 12/214,084 as of Jun. 3, 2014. filed Jun. 17, 2008. First Named Inventor, Octavian Iancea. Title, Implantable devices, systems, and methods for maintaining desired orientations in targeted tissue regions.

Woodson et al,"Multicenter study of a novel adjustable tongue-advancement device for obstructive sleep apnea," Otolaryngology and Head and Neck Surgery, Jun. 10, 2010, pp. 585-590, 143(4), Sage Publications.

Woodson et al, "Response to: Multicenter study of a novel adjustable tongue-advancement device for obstructive sleep apnea," Otolaryngology and Head and Neck Surgery, 211, pp. 1009-1010, 144(6), Sage Publications.

Hamans et al, "A novel tongue implant for tongue advancement for obstructive sleep apnea: Feasibility, safety and histology in a canine model," Journal of Musculoskeletal and Neuronal Interactions, Dec. 29, 2009, pp. 100-111, 10(1), Hylonome.

Kezirian, Eric J., M.D.,M.P.H., "Drug-Induced Sleepy Endoscopy," Dr. Kezirian's Blog, pp. 1-3, http://www.sleep-doctor.com/surgical-treatment-overview/drug-induced-sleep-endoscopy/, 2009-2014.

Medical News Today, "Aspire Medical Announces First Implant in US and Start of Clinical Trial to Treat Sleep Apnea," www.medicalnewstoday.com, May 23, 2007.

Park, Dr. Steven Y., "Aspire Medical Advance System for obstructive sleep apnea," Dr. Park: Breathe better, sleep better, live better. pp. 1-4. Oct. 6, 2010. <http://doctorstevenpark.com/aspire-medical-advance-system-for-obstructive-sleep-apnea>.

PR Newswire, "Aspire Medical appoints Roseanne Varner as president and CEO [press release]," pp. 1-2. May 1, 2011. <http://www.prnewswire.com/news-releases/aspire-medical-appoints-roseanne-varner-as-president-and-ceo-57760852.html>.

Siesta Medical, "Siesta Medical Receives 510(k) Clearance for Encore System to treat Obstructive Sleep Apnea," Siesta Medical, Los Gatos, CA, Sep. 12, 2011.

Revent Medical, "The Revent Solution: Tongue Implanter Kit," 2014. pp. 1-2, Retrieved Aug. 12, 2014. <http://www.reventmedical.com/solution/>.

Revent Medical, "The Revent Solution: Implant," 2014. pp. 1-2, Retrieved Aug. 12, 2014. <www.reventmedical.com/solution/>.

Knobbe, Martens, Olson & Bear, LLP, "Amendment and response to non-Final Office Action dated Jan. 18, 2013, for U.S. Appl. No. 13/077,813," filed Mar. 31, 2011, First Named Inventor, van der Burg. Title, Suture Passer Systems and Methods for Tongue or Other Tissue Suspension and Compression.

Synmed, "E.G. Scan: Trans-nasal, disposable system for upper GI screening," SynMed Ltd., p. 1, United Kingdom.

Mizayahi, Soichiro, M.D., et al., "A trial study of RhinoSleep for the diagnosis of sleep apnea," Psychiatry and Clinical Neuroscience, 55, pp. 249-250, 2001.

European Patent Office, Partial Supplementary European Search Report, for European Application No. 13885227.2 dated Jun. 29, 2016 p. 1-7.

European Patent Office, Extended European Search Report, for European Application No. 13885227.2 dated Oct. 5, 2016 p. 1-9.

Australian Patent Office, Examination report No. 2 for standard patent application, dated May 10, 2017.

\* cited by examiner

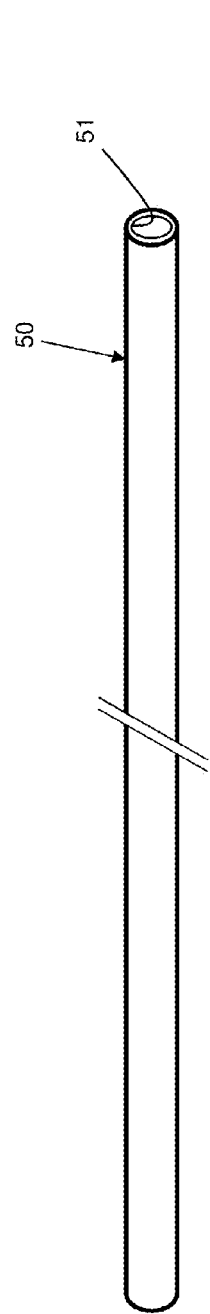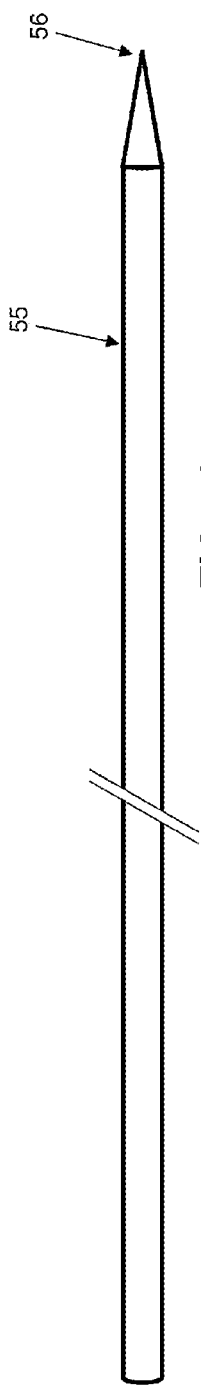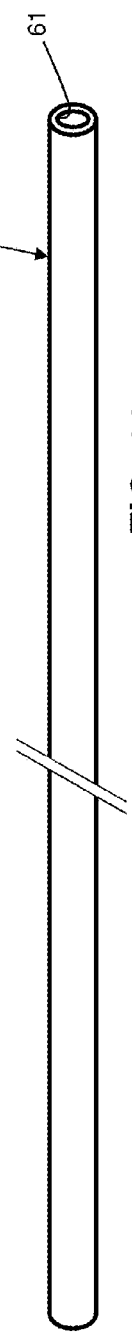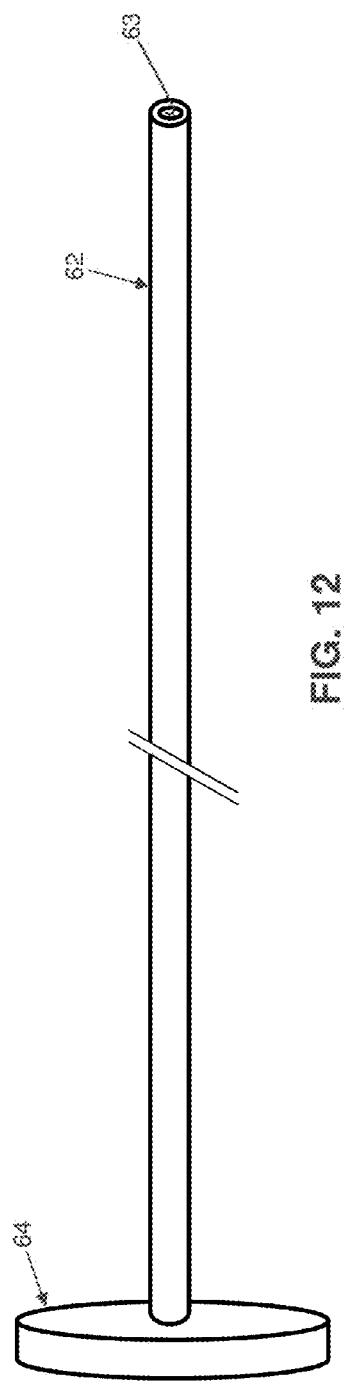

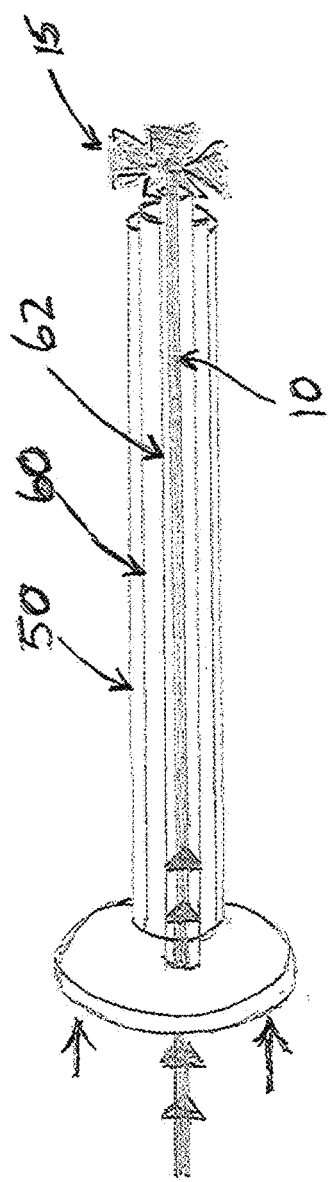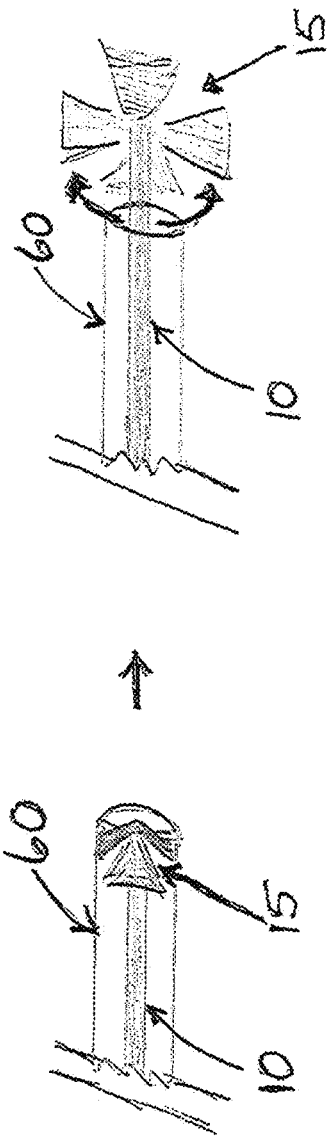
FIG. 19
FIG. 20
FIG. 21

METHOD AND APPARATUS FOR TREATING OBSTRUCTIVE SLEEP APNEA (OSA)

REFERENCE TO PENDING PRIOR PATENT APPLICATION

This patent application claims benefit of prior U.S. Provisional Patent Application Ser. No. 61/714,596, filed Oct. 16, 2012 by Peter J. Catalano for METHOD AND APPARATUS FOR TREATING OBSTRUCTIVE SLEEP APNEA (OSA), which patent application is hereby incorporated herein by reference.

FIELD OF THE INVENTION

This invention relates to surgical methods and apparatus in general, and more particularly to surgical methods and apparatus for treating obstructive sleep apnea (OSA).

BACKGROUND OF THE INVENTION

Obstructive sleep apnea (OSA) is a sleep disorder characterized by intermittent obstruction of the supralaryngeal airway. Such intermittent obstruction of the supralaryngeal airway is commonly caused by the tongue falling backward in the throat while the patient is sleeping so as to obstruct the airway. OSA typically results in significant sleep disruption, leading to excessive daytime drowsiness for the patient. OSA may also lead to cardiovascular and pulmonary disease due to the obstruction of the supralaryngeal airway, particularly where the apneal episodes last for 60 seconds or more.

Various treatments have been developed to address OSA. The more conservative treatments include prescribing weight loss to reduce tissue mass, pharmaceutical treatments, the wearing of oral appliances while sleeping, and the use of continuous positive airway pressure (CPAP) devices to maintain patency in the supralaryngeal airway. However, where such conservative treatments are not effective, or where such conservative treatments are not tolerated by the patient, a surgical procedure may be needed to prevent the tongue from obstructing the supralaryngeal airway while the patient is sleeping. Unfortunately, all of the surgical procedures developed to date suffer from one or more significant disadvantages, including poor performance, excessive trauma to the patient (e.g., the tongue and/or jaw tissue), excessive discomfort for the patient, etc.

Accordingly, a new method and apparatus is needed to treat obstructive sleep apnea (OSA).

SUMMARY OF THE INVENTION

The present invention provides a new method and apparatus for treating obstructive sleep apnea (OSA). Significantly, this new method and apparatus is minimally-invasive, whereby to minimize trauma to the patient and discomfort for the patient.

In one preferred form of the invention, there is provided apparatus for treating obstructive sleep apnea, the apparatus comprising:
a tethering device comprising:
an elastic filament having a distal end and a proximal end; and
a flexible memory head mounted to the distal end of the elastic filament.

In another preferred form of the invention, there is provided a method for treating obstructive sleep apnea, the method comprising:
providing a tethering device comprising:
an elastic filament having a distal end and a proximal end; and
a flexible memory head mounted to the distal end of the elastic filament;
advancing the tethering device through the tongue of a patient so that the flexible memory head of the tethering device is disposed against the back of the tongue and the elastic filament of the tethering device extends through the tongue; and
securing the proximal end of the elastic filament to the mandible of the patient under tension, whereby to restrain rearward movement of the tongue while the patient is sleeping.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein:

FIGS. 5-8 show further details of the head of the novel tethering device shown in FIGS. 1 and 2, wherein FIG. 5 shows the complete head, FIG. 6 shows the head with its head stiffener and overcoat removed, FIG. 7 shows the head with its head stiffener in place but the overcoat removed, and FIG. 8 shows the head stiffener alone;

FIGS. 9-12 show novel instrumentation for deploying the novel tethering device shown in FIGS. 1 and 2;

FIGS. 13-33 show one preferred method (and associated apparatus) for deploying the novel tethering device shown in FIGS. 1 and 2 using the novel instrumentation shown in FIGS. 9-12;

DETAILED DESCRIPTION OF THE PREFERRED EMBODIMENTS

The present invention provides a new method and apparatus for treating obstructive sleep apnea (OSA). Significantly, this new method and apparatus is minimally-invasive, whereby to minimize trauma to the patient and discomfort for the patient.

Figure 1:
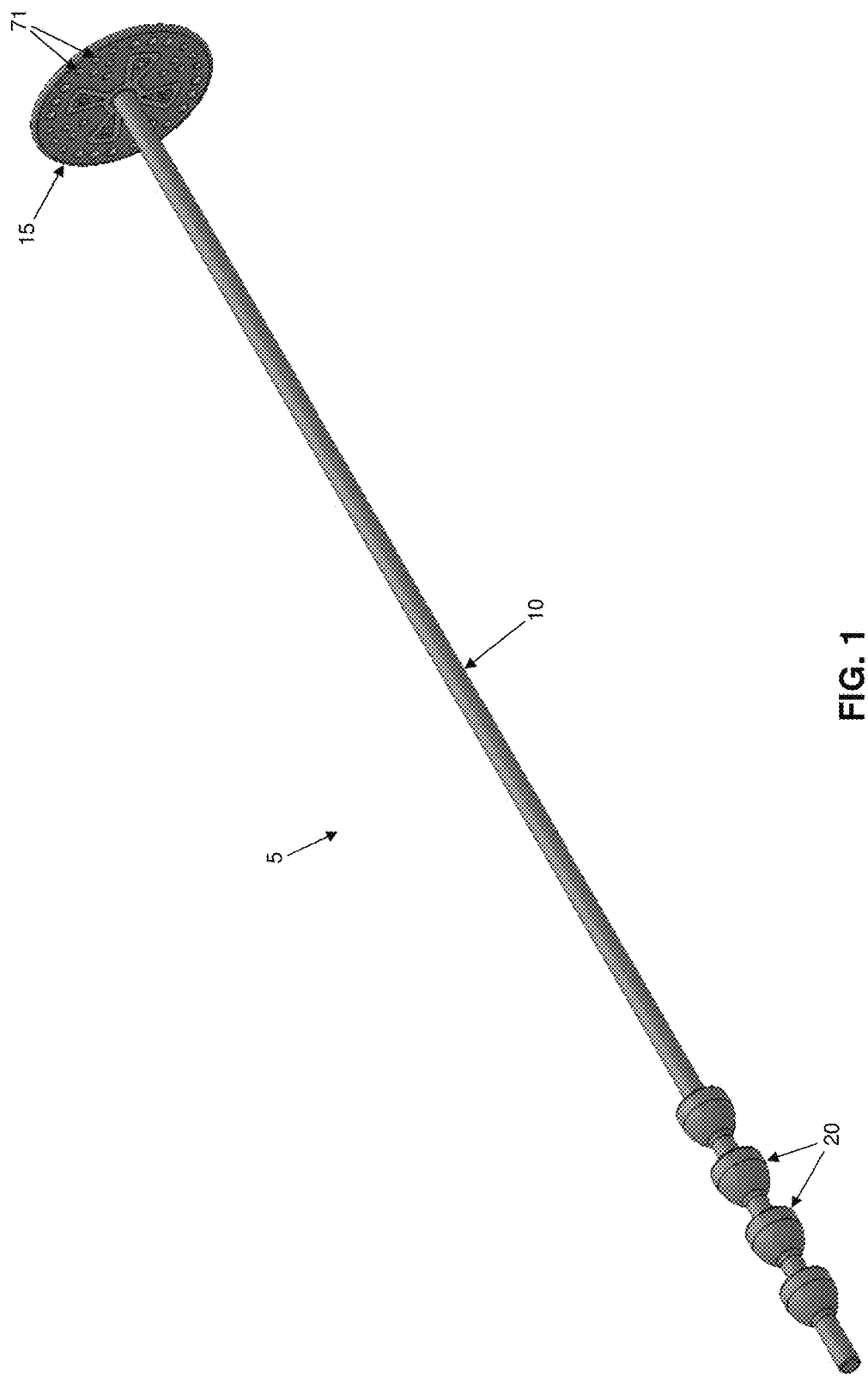
FIGS. 1 and 2 are schematic views showing a novel tethering device formed in accordance with the present invention.
Figure 2:
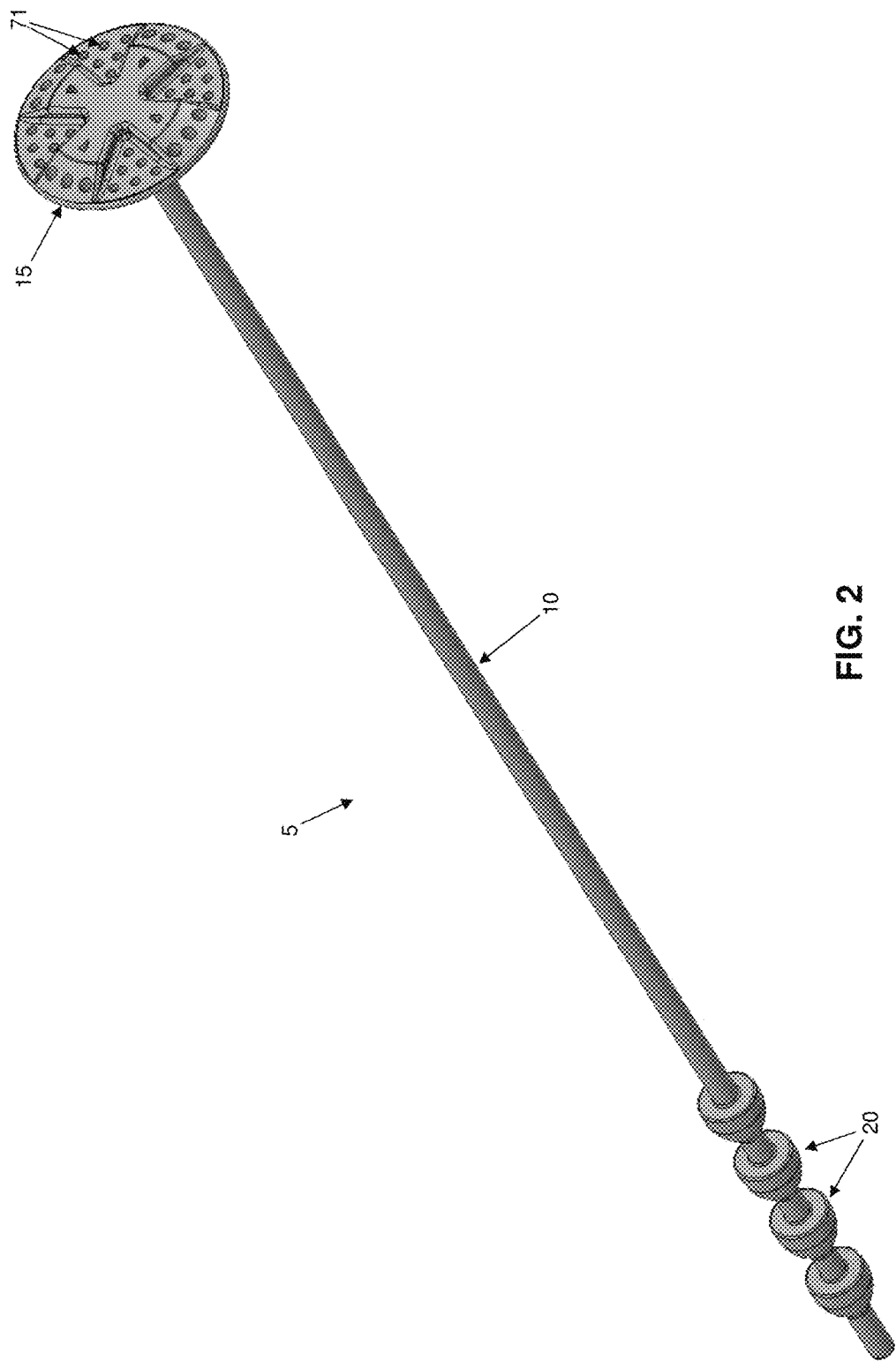

More particularly, in accordance with the present invention, and looking now at FIGS. 1 and 2, there is provided a novel tethering device 5 for restraining rearward movement of the tongue so as to prevent the tongue from obstructing the supralaryngeal airway while the patient is sleeping, whereby to treat obstructive sleep apnea. As seen in FIGS. 1 and 2, tethering device 5 generally comprises an elastic filament 10 having a head 15 on its distal end and a series of enlargements 20 (e.g., frustoconical enlargements) on its proximal end.

Figure 3:
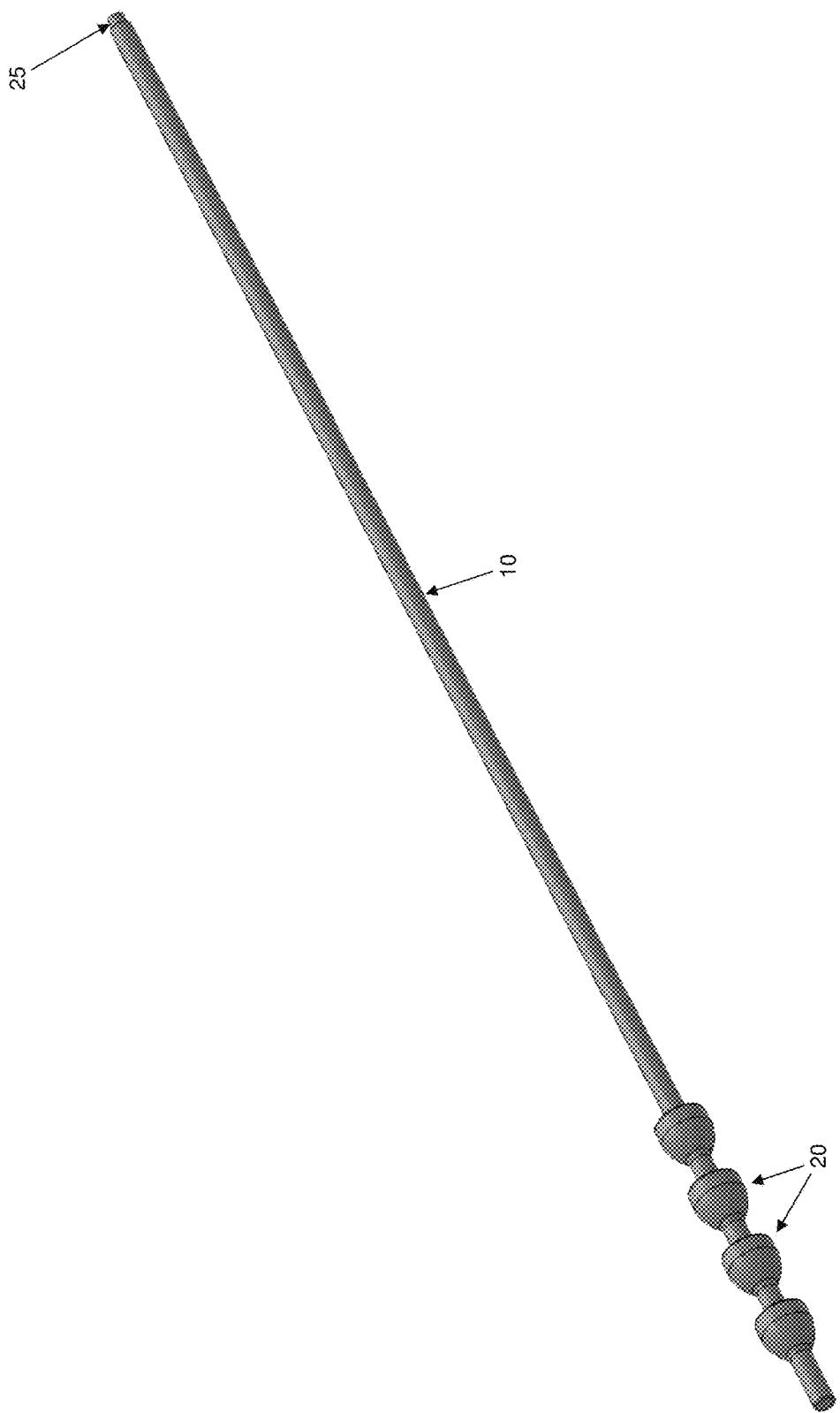
FIGS. 3 and 4 show further details of the elastic filament of the novel tethering device shown in FIGS. 1 and 2.
Figure 4:
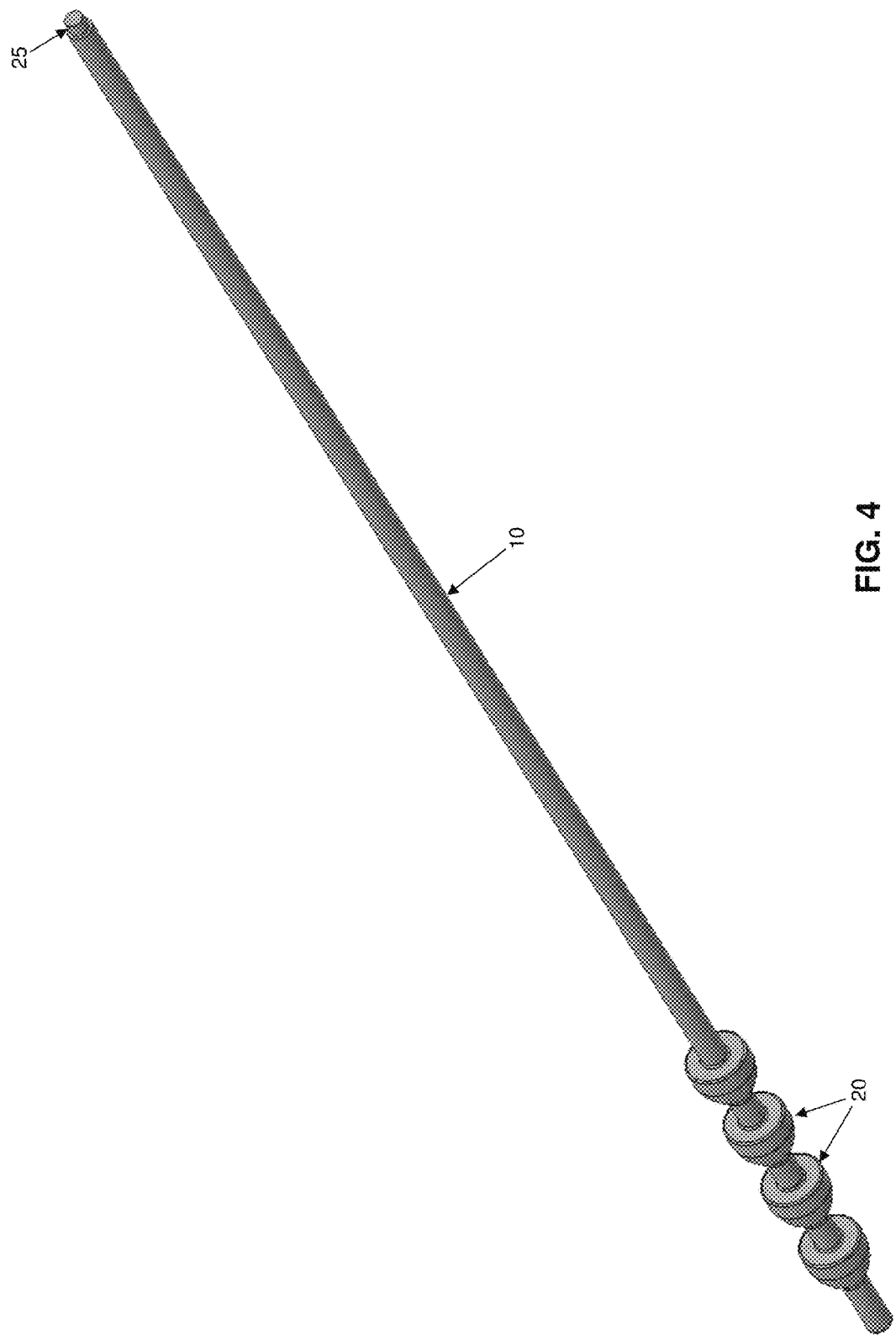
Figure 5:
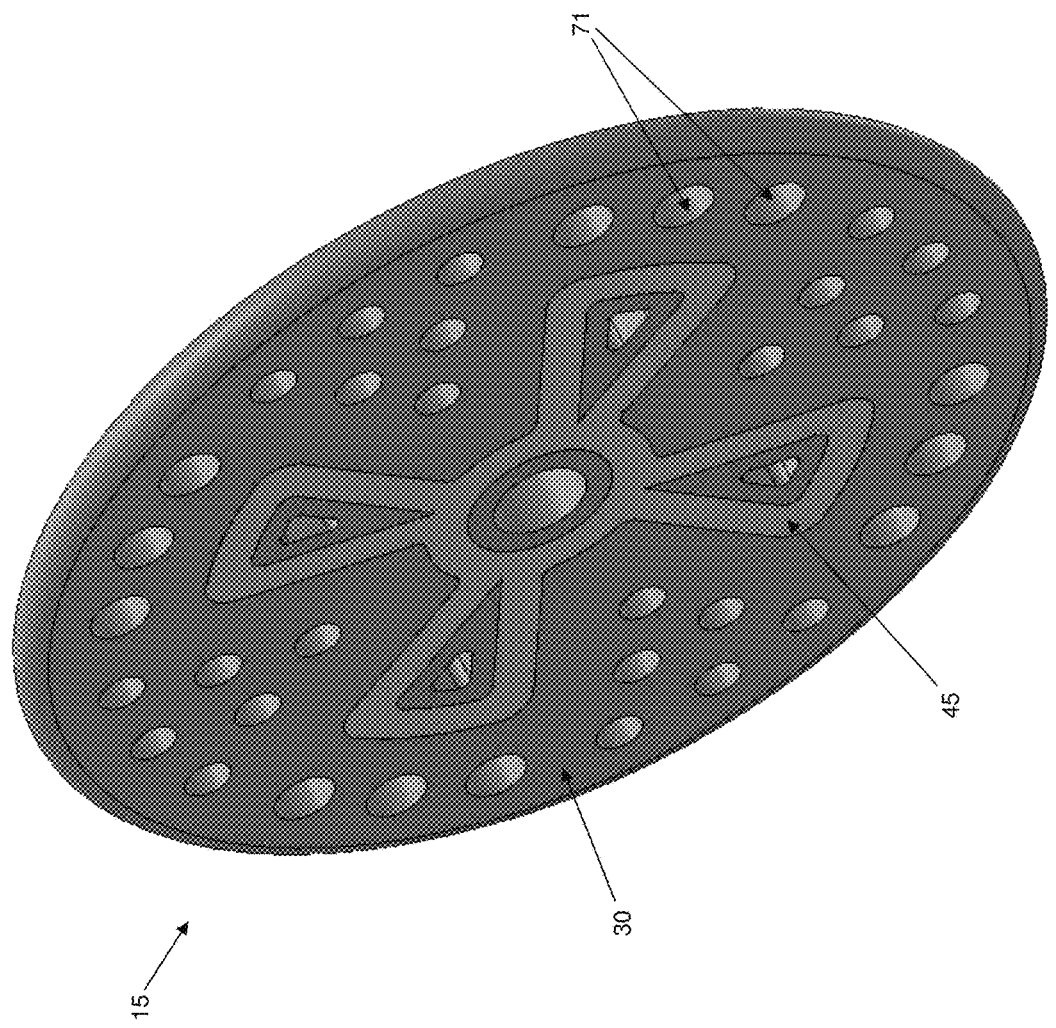
Figure 6:
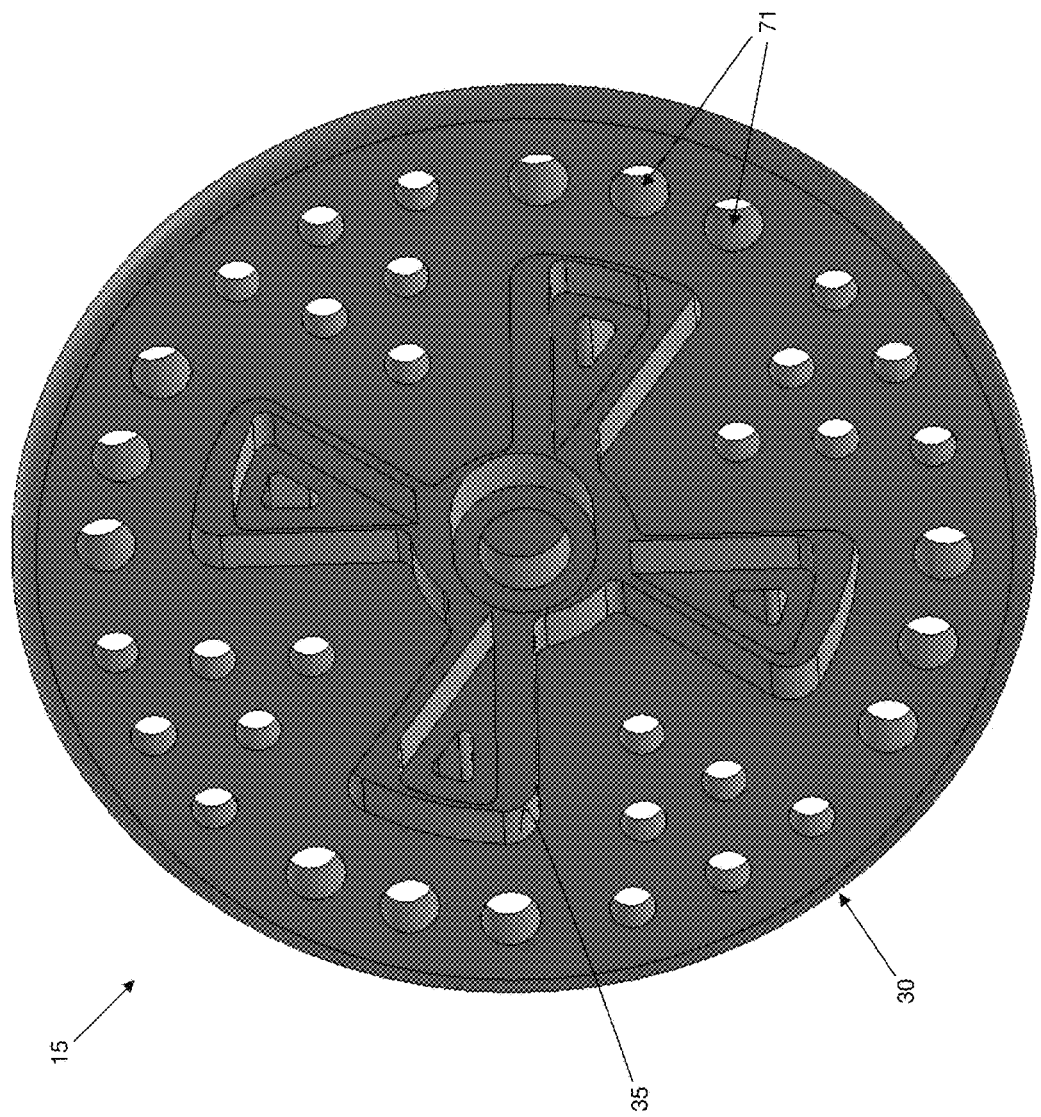
Figure 7:
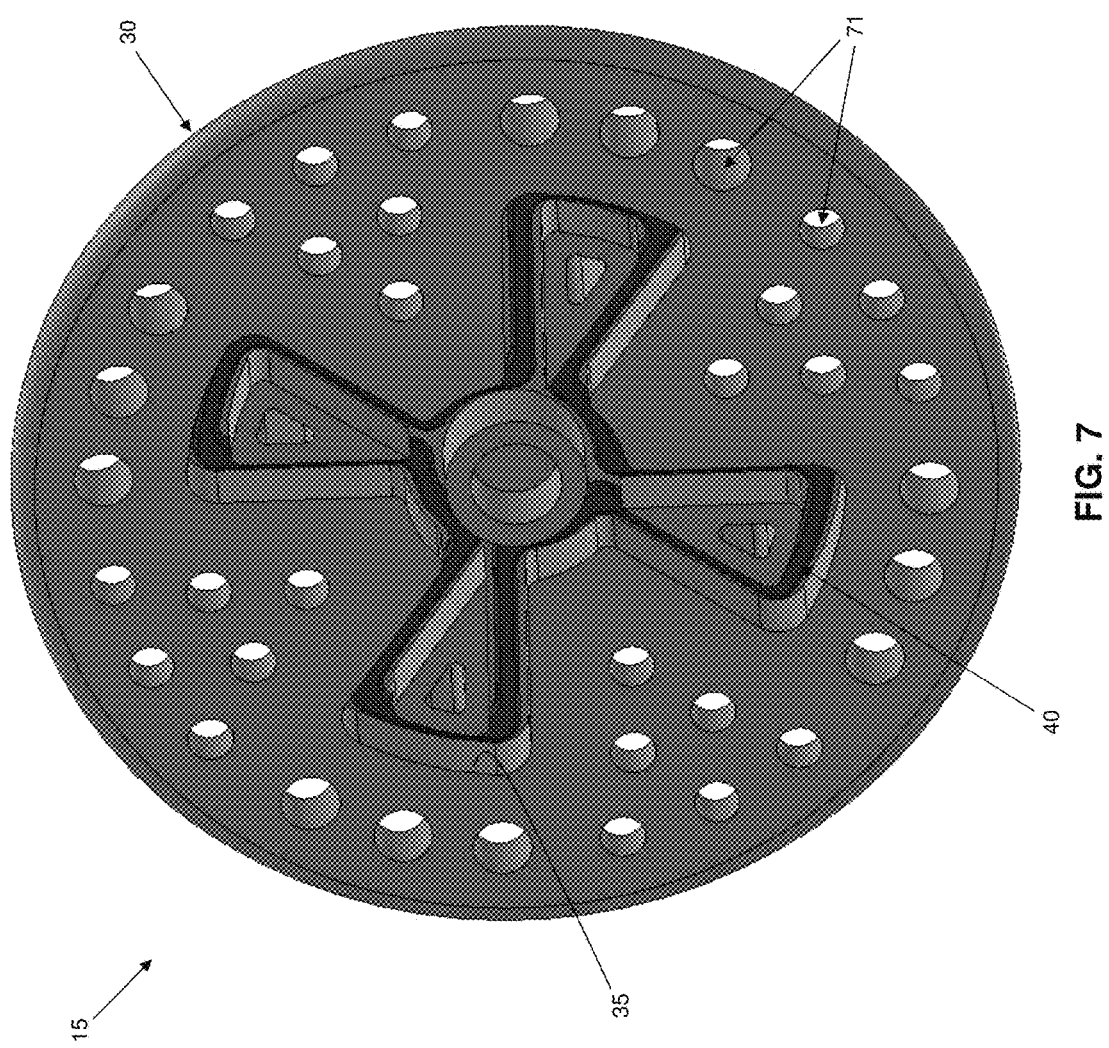
Figure 8:
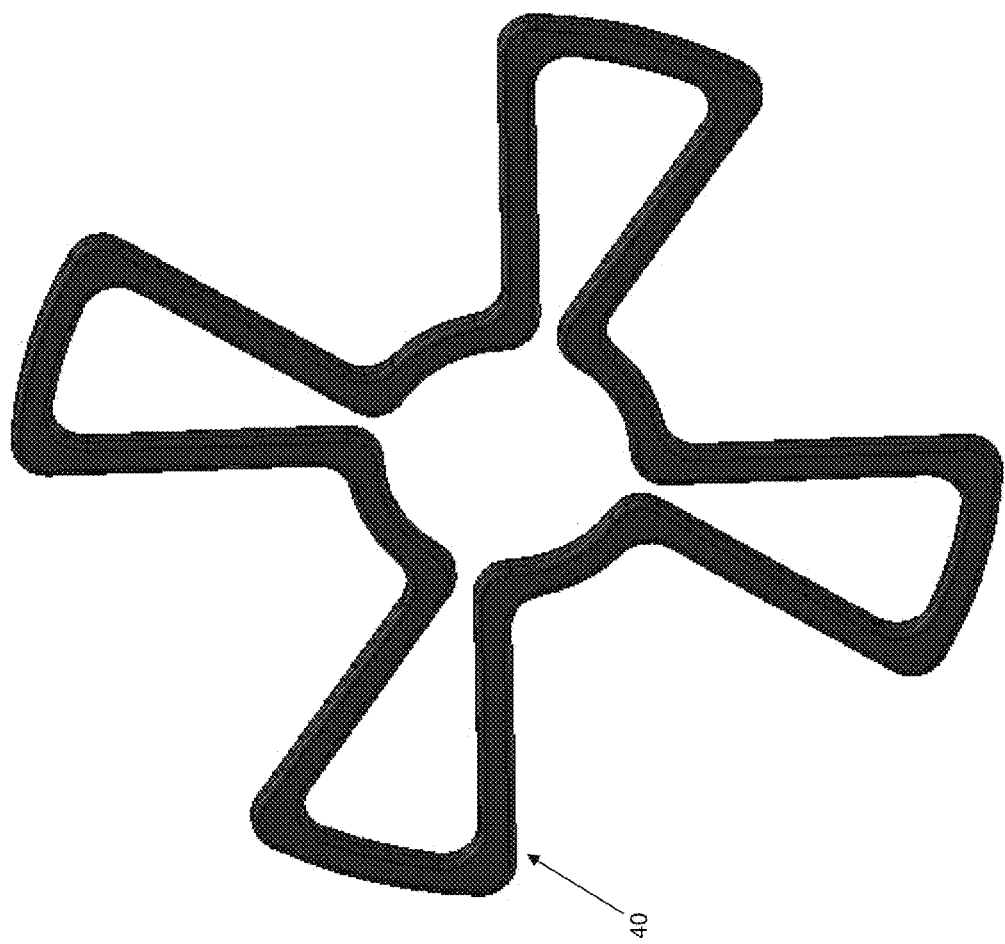

FIGS. 3 and 4 show further details of elastic filament 10. In general, elastic filament 10 comprises an elastomeric material having means 25 on its distal end for mounting head 15 to the distal end of the filament, and the aforementioned enlargements 20 (e.g., frustoconical enlargements) on its proximal end. As will hereinafter be discussed, enlargements 20 (disposed on the proximal end of elastic filament 10) facilitate securing the proximal end of elastic filament 10 to a bone anchor secured to the lower mandible of the patient, as will hereinafter be discussed in further detail.

FIGS. 5-8 show further details of head 15. In general, head 15 comprises a large disk-like structure 30 (FIG. 5) formed out of a relatively soft, pliable, atraumatic material. This large disk-like structure 30 has a patterned recess 35 (FIG. 6) formed in its proximal side for receiving a head stiffener 40 (FIGS. 7 and 8), whereby to provide head 15 with appropriate structural integrity for its intended purpose (i.e., to provide a bearing structure at the back of the tongue so as to allow tethering device 5 to restrain rearward movement of the tongue, as will hereinafter be discussed). An overcoat 45 (FIG. 5) is set atop head stiffener 40 so as to seal head stiffener 40 within patterned recess 35 of the large disk-like structure 30. In one preferred form of the invention, patterned recess 35 and head stiffener 40 each have a multi-lobe configuration (e.g., four lobes as shown, or three lobes, or two lobes, or five lobes, etc.). And, in one preferred form of the invention, head stiffener 40 is preferably formed out of superelastic material, e.g., Nitinol or another superelastic metal alloy, whereby to permit head stiffener 40 to be significantly deformed and thereafter elastically re-form, as will hereinafter be discussed. It will be appreciated that, on account of the foregoing construction, head 15 effectively comprises a flexible memory structure disposed at the distal end of elastic filament 10, and this flexible memory head provides a sufficient bearing structure to restrain rearward movement of the tongue, as will hereinafter be discussed.

Looking now at FIGS. 9-12, there is shown preferred instrumentation for deploying tethering device 5 in the anatomy of a patient. In general, this instrumentation comprises a corridor sheath 50 having a lumen 51 extending therethrough (FIG. 9), a corridor trocar 55 terminating in a sharp distal tip 56 (FIG. 10), an outer inserter tube 60 having a lumen 61 extending therethrough (FIG. 11), and an inner inserter tube 62 having a lumen 63 extending therethrough and having a head 64 attached to its proximal end. As will hereinafter be discussed below, corridor trocar 55 is sized to fit within lumen 51 of corridor sheath 50, outer inserter tube 60 is sized to fit within lumen 51 of corridor sheath 50, inner inserter tube 62 is sized to fit within lumen 61 of outer inserter tube 60, and lumen 63 of inner inserter tube 62 is sized to receive the elongated body (sometimes hereinafter referred to as the "shaft") of elastic filament 10.

Figure 13:
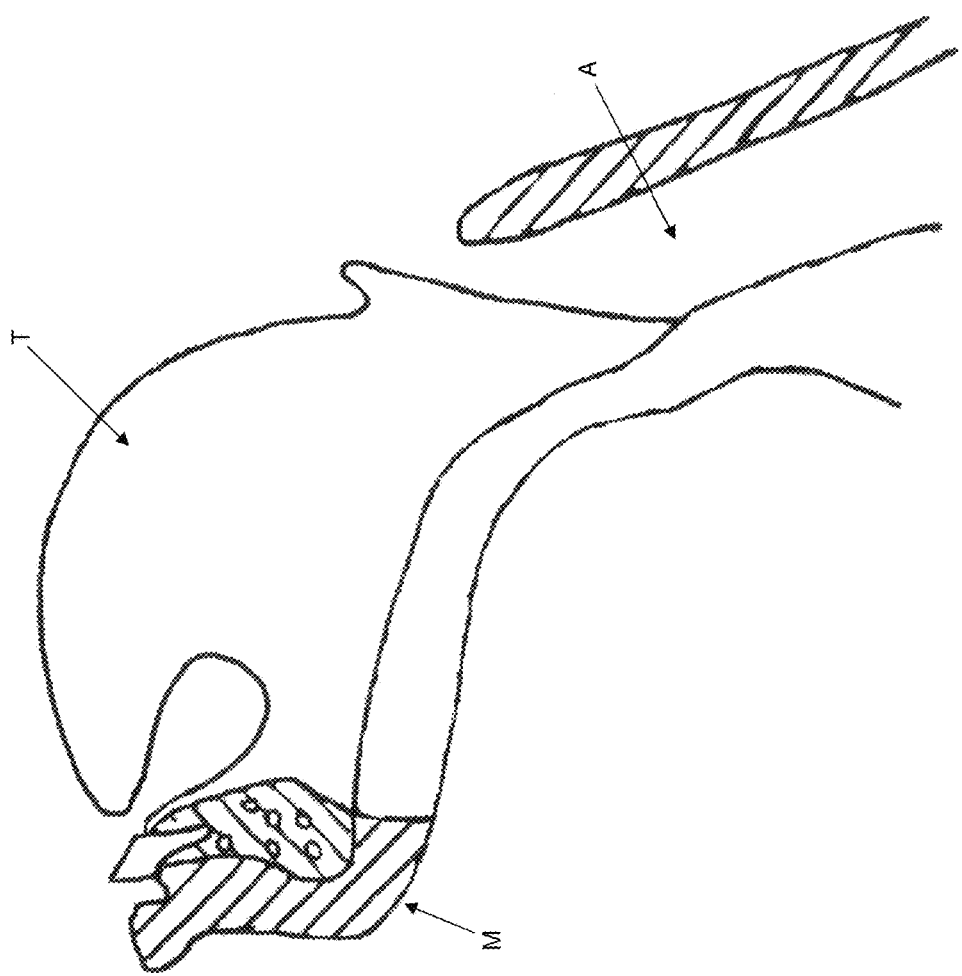

The novel tethering device 5 of FIGS. 1-8 is intended to be deployed in the native anatomy of a patient (FIG. 13), preferably using the corridor sheath 50, corridor trocar 55, outer inserter tube 60 and inner inserter tube 62 of FIGS. 9-12, so as to restrain rearward movement of the tongue T and thereby prevent tongue T from obstructing the supralaryngeal airway A of the patient while the patient is sleeping, whereby to treat obstructive sleep apnea. Also shown in FIG. 13 is the lower mandible M of the patient.

Figure 14:
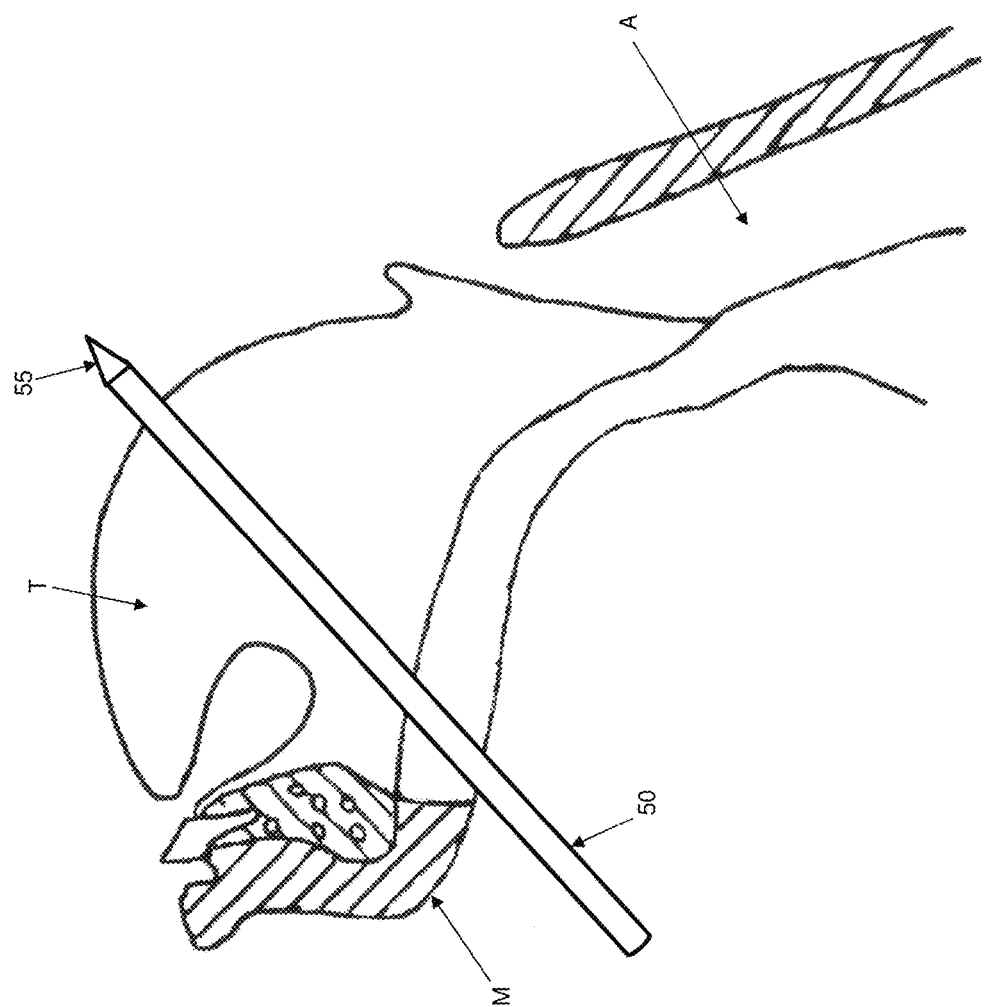

More particularly, and looking now at FIG. 14, corridor sheath 50, having corridor trocar 55 disposed therein so that the sharp distal tip 56 of corridor trocar 55 extends out the distal end of corridor sheath 50, is inserted upward and backward through tongue T. Distal movement of the assembled corridor sheath 50/corridor trocar 55 continues until the distal end of corridor sheath 50 emerges through the back of tongue T.

Figure 15:
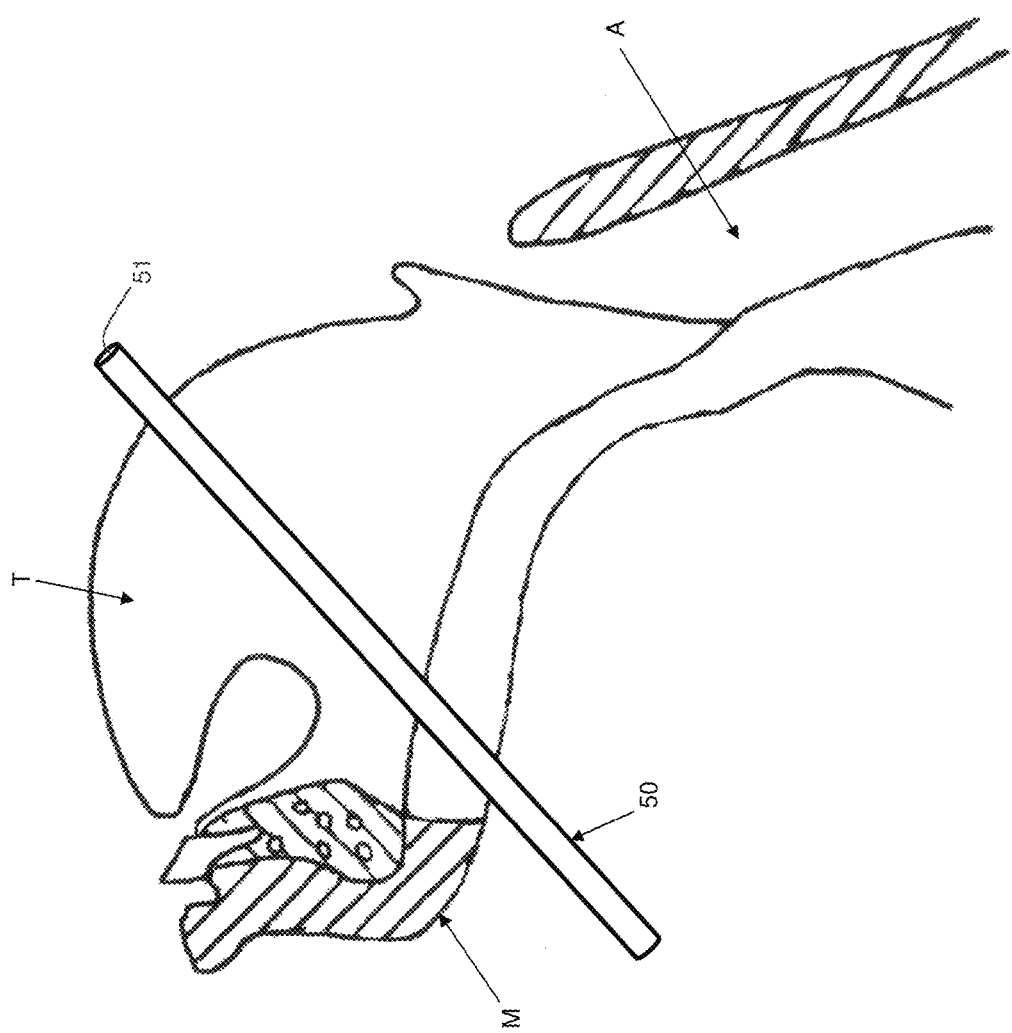

Then corridor trocar 55 is removed, from posterior to anterior (i.e., proximally), leaving corridor sheath 50 extending upward and backward through tongue T, in the manner shown in FIG. 15.

Next, outer inserter tube 60 and inner inserter tube 62 are used to advance tethering device 5 through lumen 51 of the emplaced corridor sheath 50.

Figure 16:
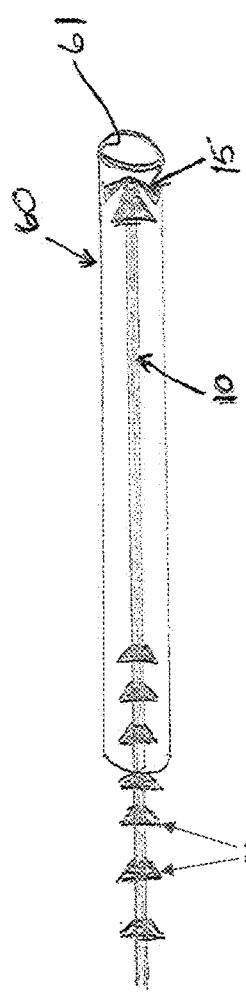
Figure 17:
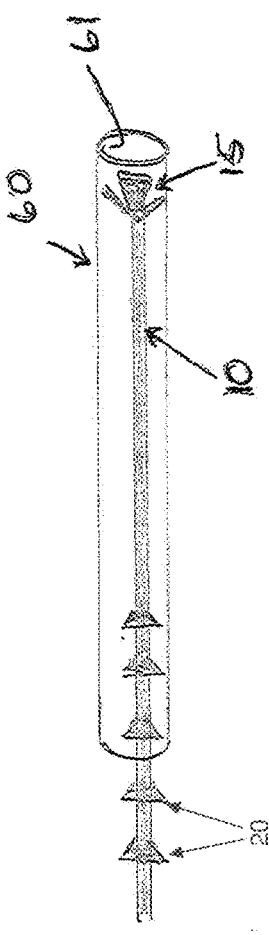
Figure 18:
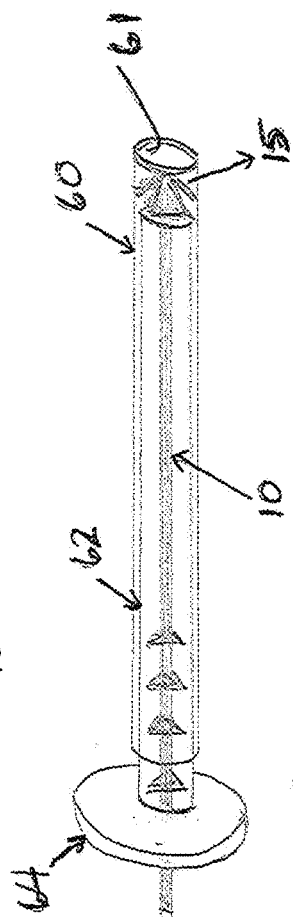

More particularly, tethering device 5 is loaded into outer inserter tube 60 by folding head 15 towards the proximal end of the "shaft" of elastic filament 10 so that the lobes of head 15 are substantially aligned with, and substantially parallel to, the shaft of elastic filament 10 (FIG. 16), or folding head 15 away from the proximal end of the shaft of elastic filament 10 so that they fold onto themselves and extend beyond the distal end of the shaft of elastic filament 10 (FIG. 17). Then inner inserter tube 62 is slid over the proximal end of elastic filament 10 of tethering device 5, in a distal-to-proximal direction, until the folded head 15 of tethering device 5 is contacted and engaged by the distal end of inner inserter tube 62 (FIG. 18). It will be appreciated that, at this point, head 15 of tethering device 5 is folded and housed within outer inserter tube 60 and the shaft of elastic filament 10 extends back through lumen 63 of inner inserter tube 62 (which is itself disposed within lumen 61 of outer inserter tube 60).

It will be appreciated that as a result of the foregoing construction and assembly, if and when head 64 of inner inserter tube 62 should thereafter be moved distally relative to outer inserter tube 60, the folded head 15 of elastic filament 10 will be ejected out of the distal end of outer inserter tube 60, whereby to deploy head 15 to its original pre-folded shape (FIGS. 19-21).

It should be appreciated that the assembly shown in FIG. 18 may be assembled at the time of use (e.g., on a "back table" in an operating room) or at the time of manufacture (in which case it is packaged and shipped in the form shown in FIG. 18).

Figure 22:
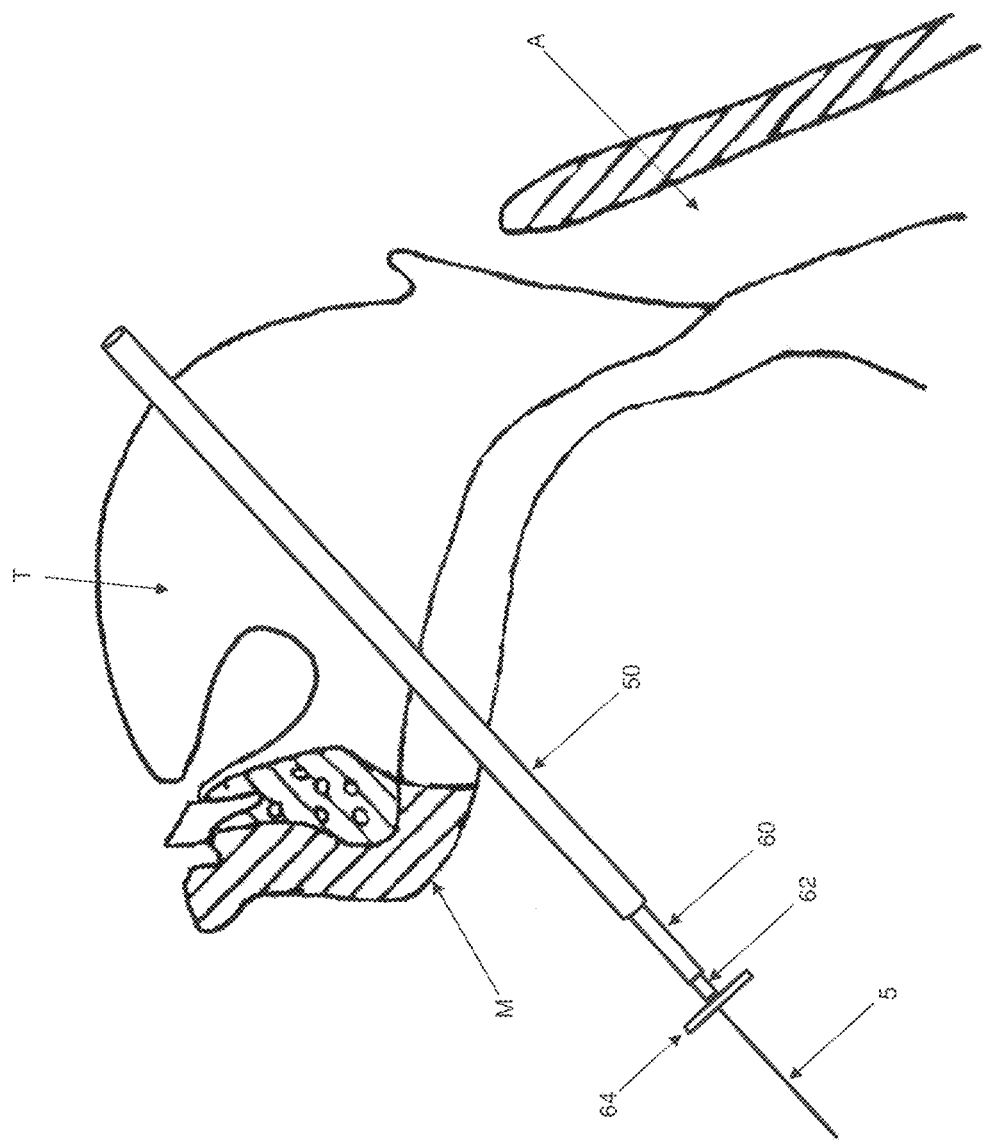

This "tube-over-tube" assembly (FIG. 18) allows tethering device 5 to be quickly and easily advanced through lumen 51 of the emplaced corridor sheath 50 (FIG. 15), such that tethering device 5 can be properly positioned in the patient. More particularly, with head 15 of tethering device 5 folded and housed within lumen 61 of outer inserter tube 60, and with the shaft of elastic filament 10 extending back through lumen 63 of inner inserter tube 62, the assembly of outer inserter tube 60, tethering device 5, and inner inserter tube 62 is inserted into the proximal end of lumen 51 of corridor sheath 50 and then advanced, in a proximal-to-distal manner (FIG. 22).

Figure 23:
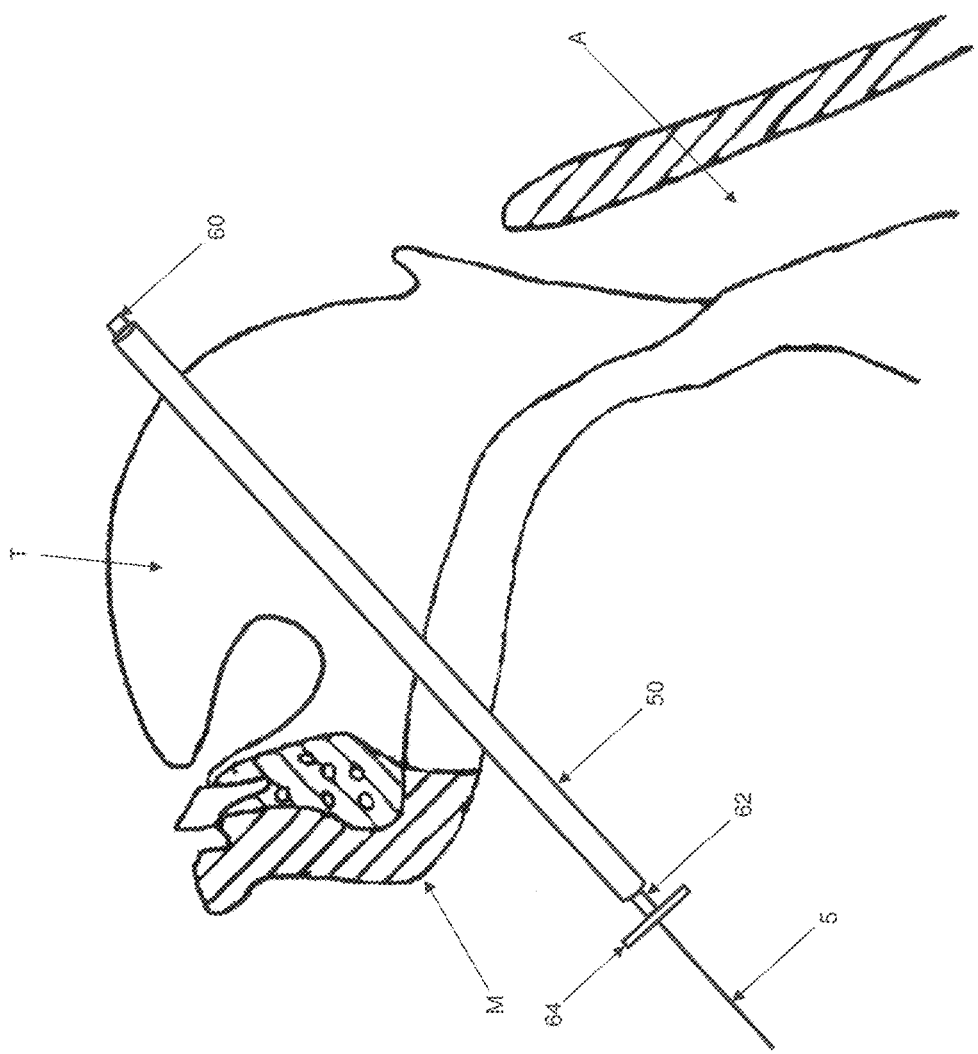

This proximal-to-distal movement continues until the distal end of outer inserter tube 62 emerges from the distal end of corridor sheath 50 on the back side of the tongue (FIG. 23).

Figure 24:
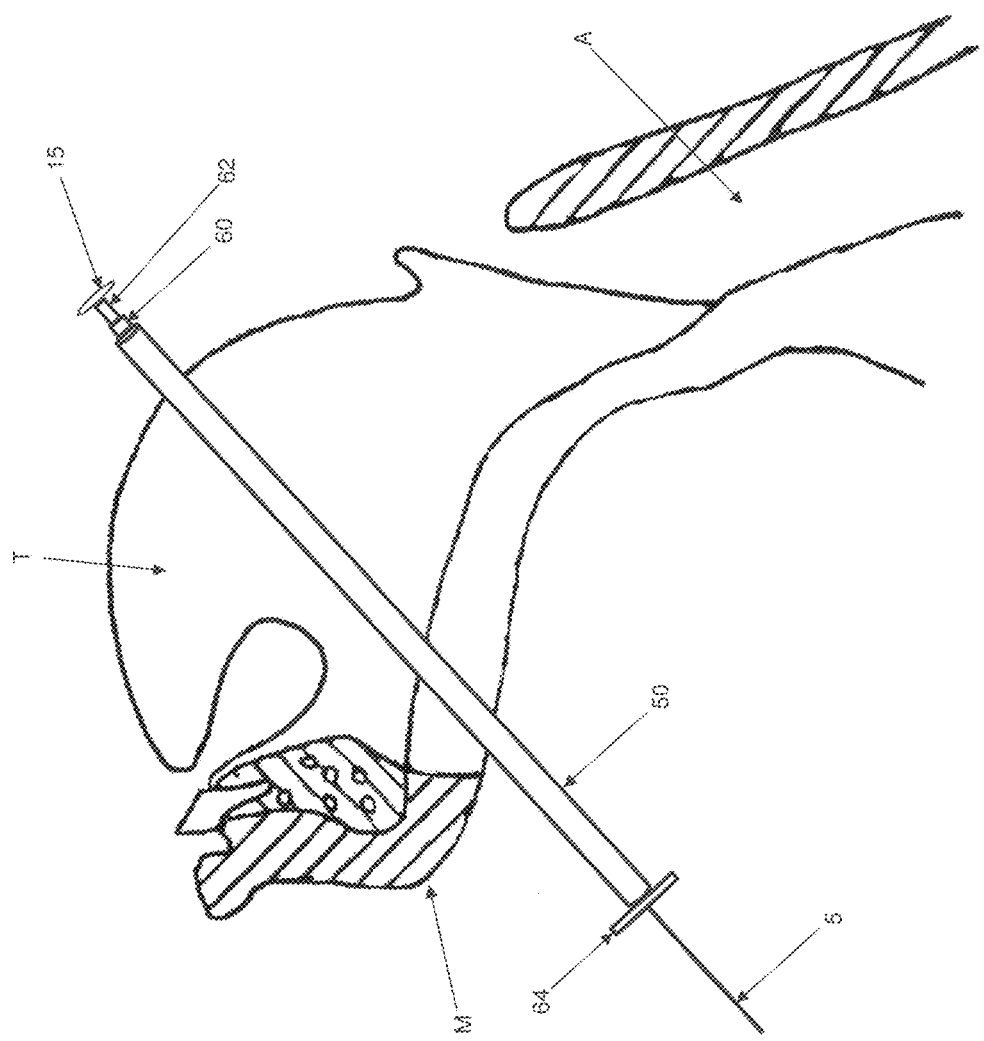

Then head 64 of inner inserter tube 62 is moved further distally until it rests against the proximal end of corridor sheath 50 (FIG. 24), causing the folded head 15 to emerge from the distal end of outer inserter tube 60, whereupon head 15 will unfold back to its original pre-folded shape due to the memory effects of stiffener 40 in head 15 (FIG. 24).

In this respect it will be appreciated that by forming head stiffener 40 out of a superelastic material (e.g., Nitinol or another superelastic metal alloy), the folding of head 15 in outer inserter tub 60 is facilitated, and the unfolding of head 15 as it emerges from the distal end of outer inserter tube 60 will also be facilitated.

In other words, outer inserter tube 60 and inner inserter tube 62 are used together to advance the folded head 15 of tethering device 5 through corridor sheath 50 (and hence through tongue T), with the head 15 of the tethering device being held in a folded condition within outer inserter tube 60 until the distal end of outer inserter tube 60 emerges from the distal end of corridor sheath 50. Inner inserter tube 62 is then used to eject folded head 15 out of the distal end of outer inserter tube 60, whereupon folded head 15 unfolds, with the unfolded head 15 residing on the far side of tongue T.

Once head 15 is unfolded and deployed on the far side of tongue T, inner inserter tube 62 and outer inserter tube 60 are withdrawn proximally back through corridor sheath 50, leaving elastic filament 10 extending back through lumen 51 of corridor sheath 50 (and hence elastic filament 10 extending back through tongue T).

Figure 25:
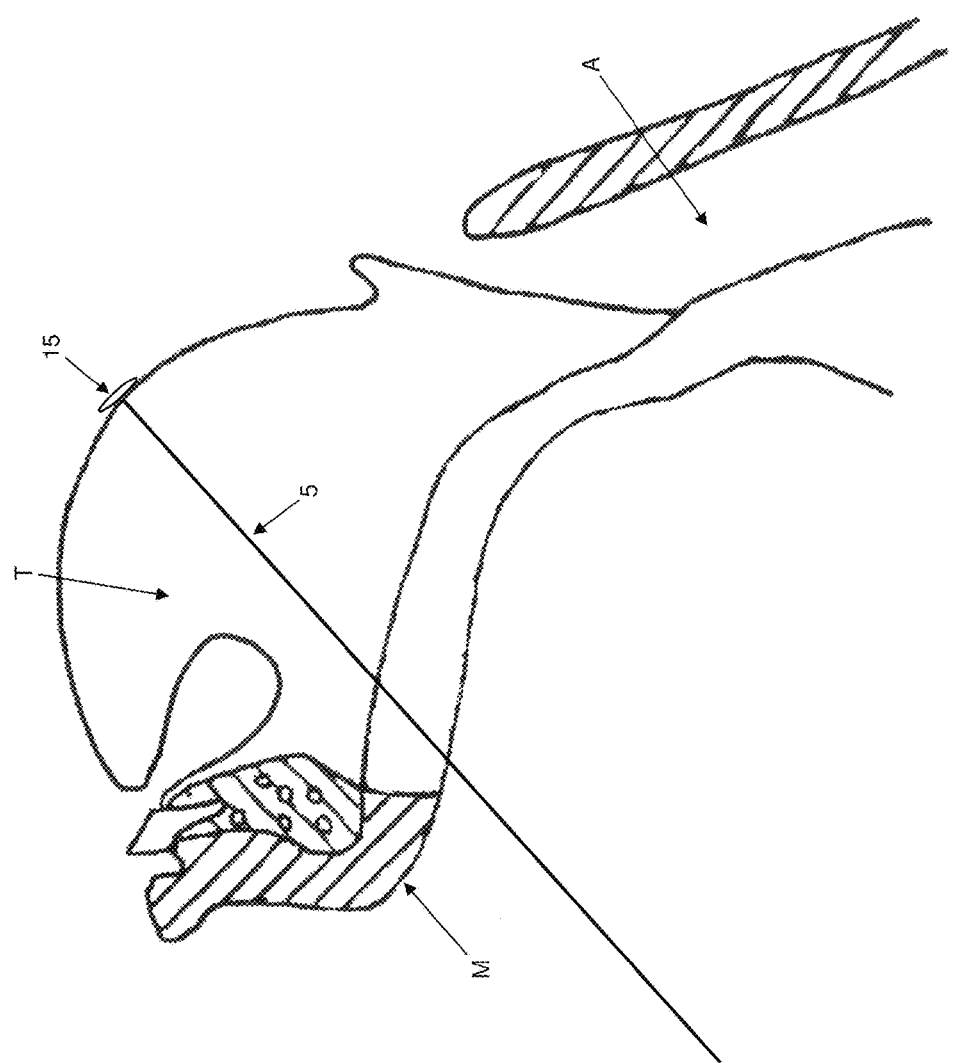

Then corridor sheath 50 is removed, leaving tethering device 5 extending through tongue T, with head 15 of tethering device 5 sprung open adjacent the back of tongue T (FIG. 25).

Figure 26:
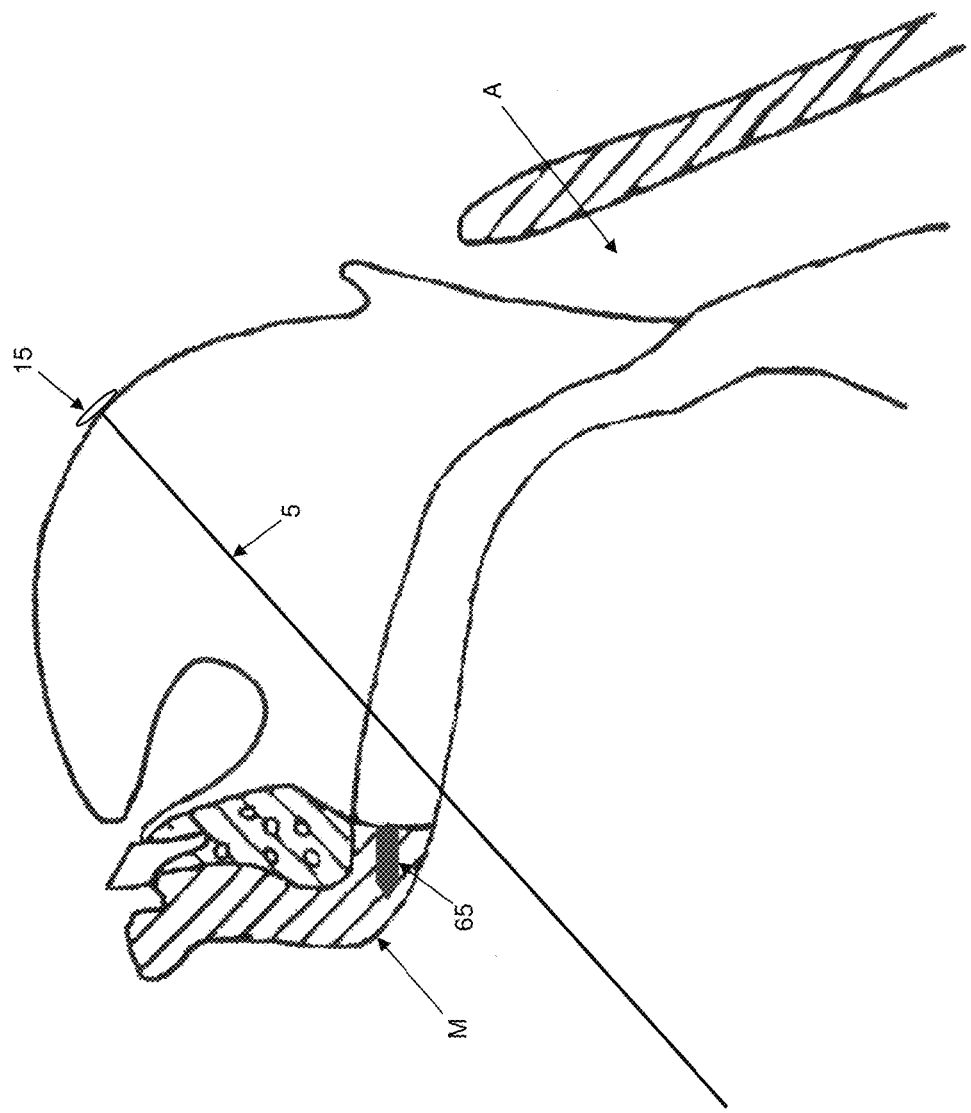
Figure 27:
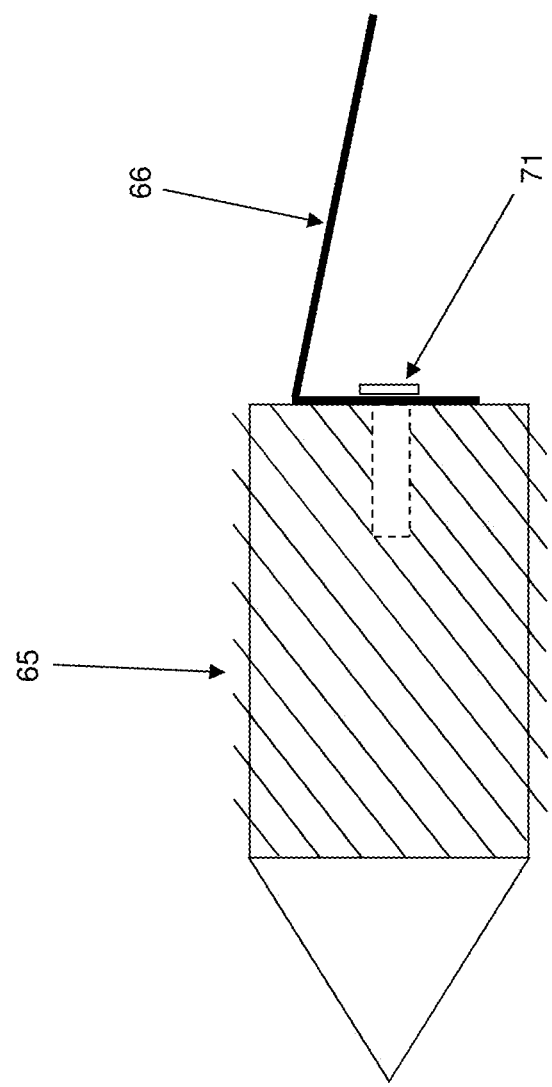
Figure 28:
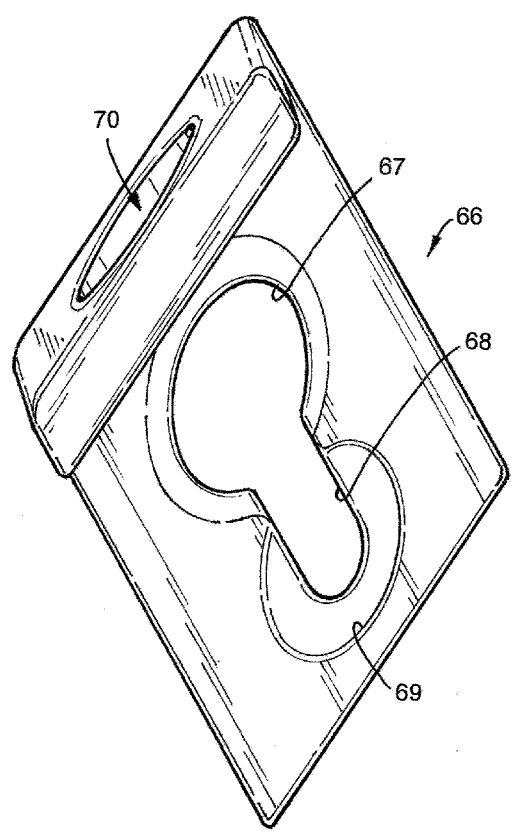
Figure 29:
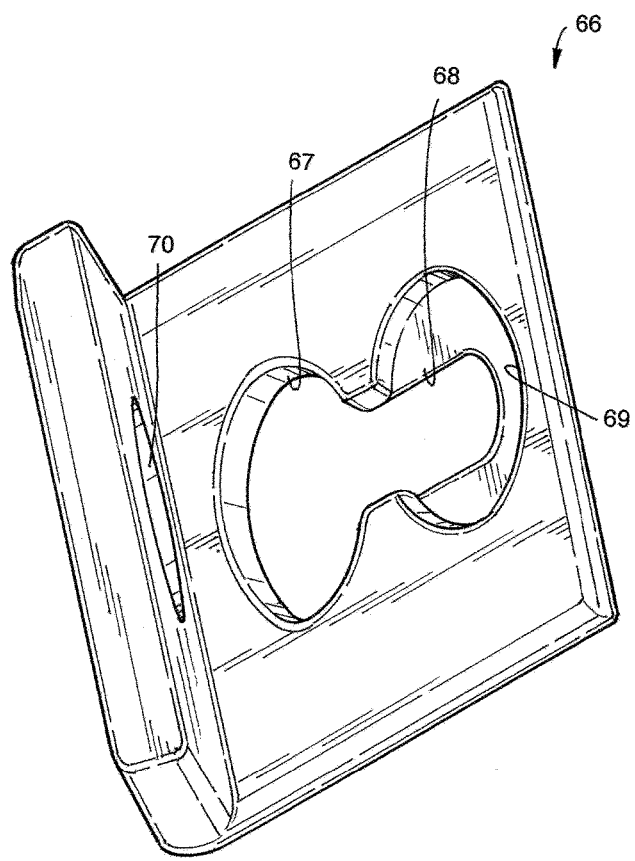
Figure 30:
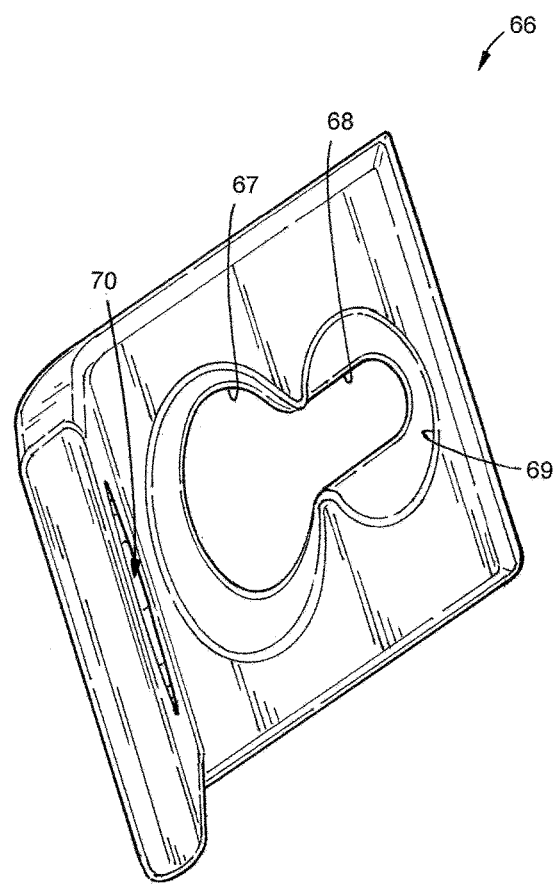
Figure 31:
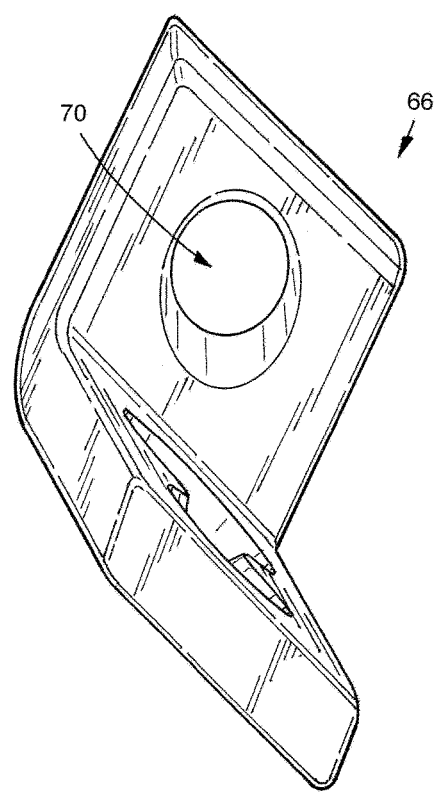
Figure 32:
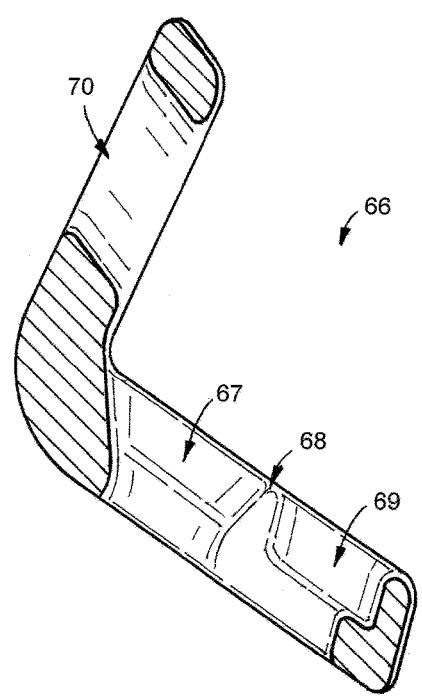

Next, a bone anchor 65 is deployed in the lower mandible M (FIG. 26). Bone anchor 65 may be a so-called screw-type bone anchor or another type of bone anchor (e.g., a barb-type bone anchor, etc.). As seen in FIGS. 27-32, bone anchor 65 preferably includes a mount 66 for mounting the proximal end of elastic filament 10 to the bone anchor. Mount 66 preferably has a hole 67 and a slot 68 formed therein. A seat 69 is preferably formed at the end of slot 68. Mount 66 preferably also includes a hole 70 for securing mount 66 to bone anchor 65 via screw 73. Mount 66 may be mounted to bone anchor 65 either before bone anchor 65 is deployed in mandible M or after bone anchor 65 has been deployed in mandible M.

Figure 33:
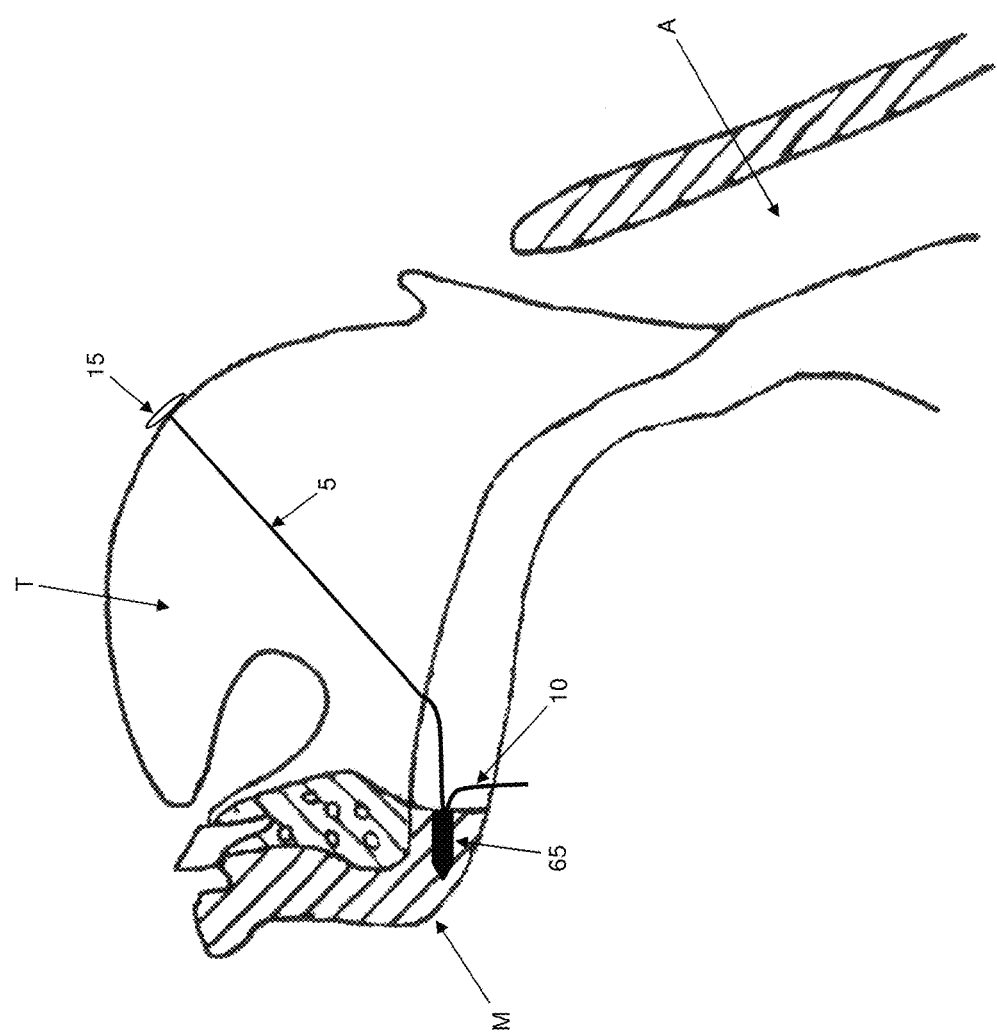
Figure 34:
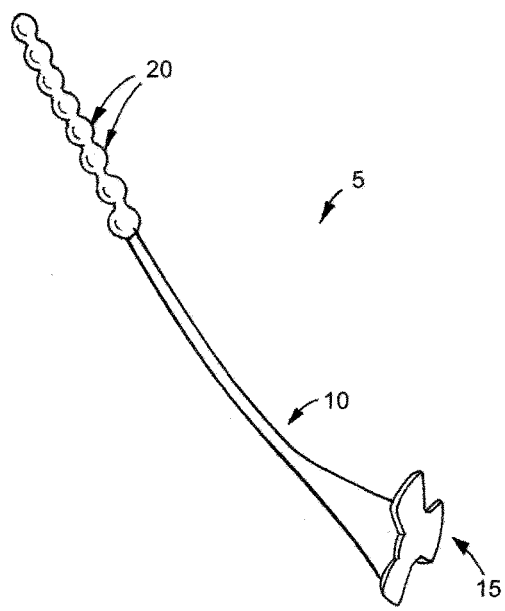
FIGS. 34-36 show an alternative head for the novel tethering device shown in FIGS. 1 and 2.

After bone anchor 65 (and mount 66) have been secured to lower mandible M, elastic filament 10 of tethering device 5 is secured to mount 66 of bone anchor 65 under tension (FIG. 33) so that head 15 of tethering device 5 is pulled flush against the back surface of the tongue and supports the tongue from backward displacement when at rest. More particularly, elastic filament 10 of tethering device 5 is secured to bone anchor 65 by passing enlargements 20 (e.g., frustoconical enlargements) on the proximal end of filament 10 through hole 67 of mount 66 and then moving filament 10 laterally along slot 68 so as to seat an enlargement 20 in seat 69 of mount 66.

It will be appreciated that, as a result of the foregoing, tethering device 5 essentially elastically tethers the back of tongue T to a fixed anatomic point (i.e., the lower mandible M, where bone anchor 65 is set) using an elastic filament 10 terminating in an atraumatic head 15. With tongue T tethered in this manner, normal function of the tongue is retained (e.g., during talking and swallowing), yet rearward movement of the tongue is restrained while the patient is sleeping, thereby preventing the tongue from obstructing the supralaryngeal airway A while the patient is sleeping, and thus treating obstructive sleep apnea. And by forming head 15 out of a relatively soft, pliable, atraumatic material, reinforced by an internal head stiffener 40, head 15 will provide the necessary structural integrity while being atraumatic to the tissue. Furthermore, by virtue of the low profile of head 15 vis-à-vis the back of the tongue, the head of the tethering device does not interfere with swallowing action or breathing.

In the preferred form of the invention, and looking now at FIGS. 1, 2 and 5-7, a plurality of holes 71 are formed on the large disk-like structure 30 of head 15. Holes 71 can be advantageous in the event that the tethering device 5 should fail and head 15 should be aspirated, since holes 71 can prevent head 15 from completely obstructing an air passageway (which may sometimes also be referred to as an "airway").

Figure 35:
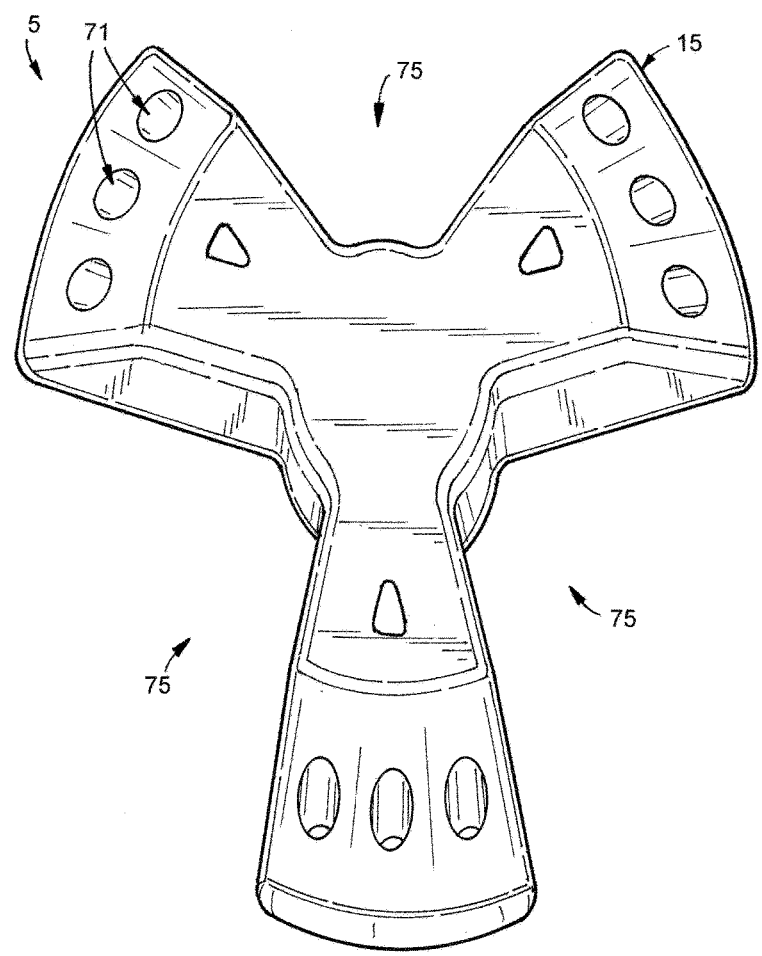
Figure 36:
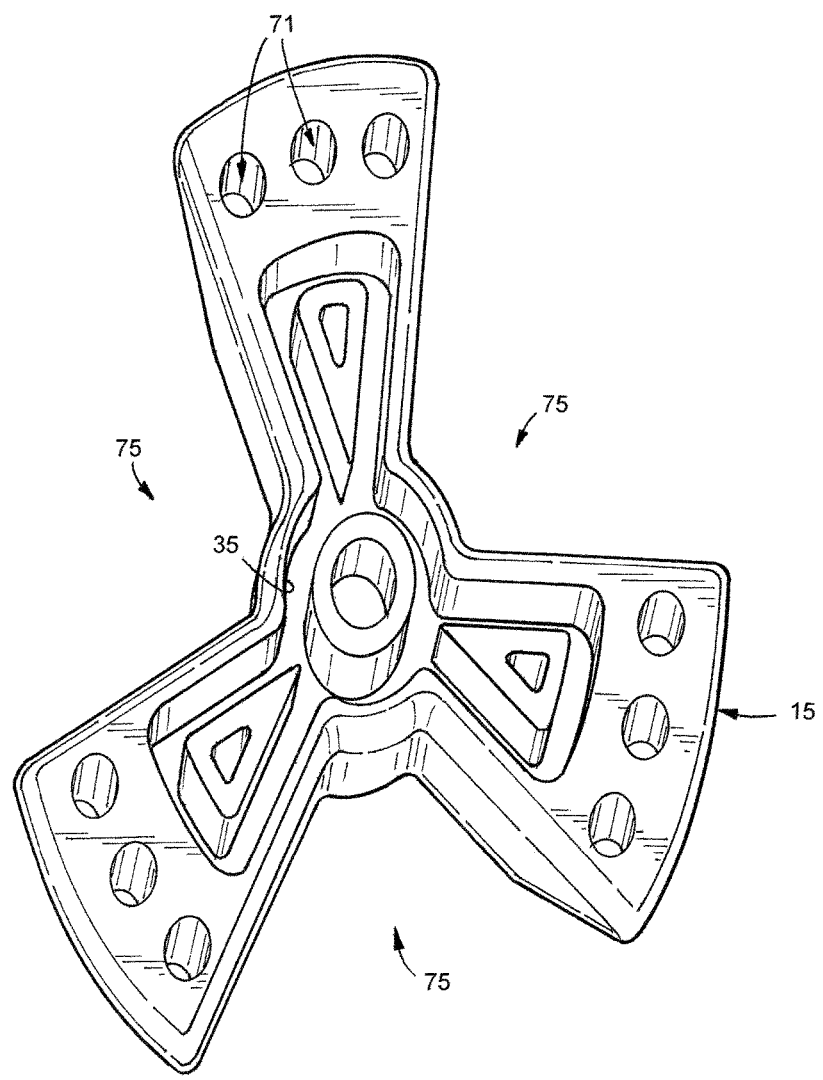
Figure 37:
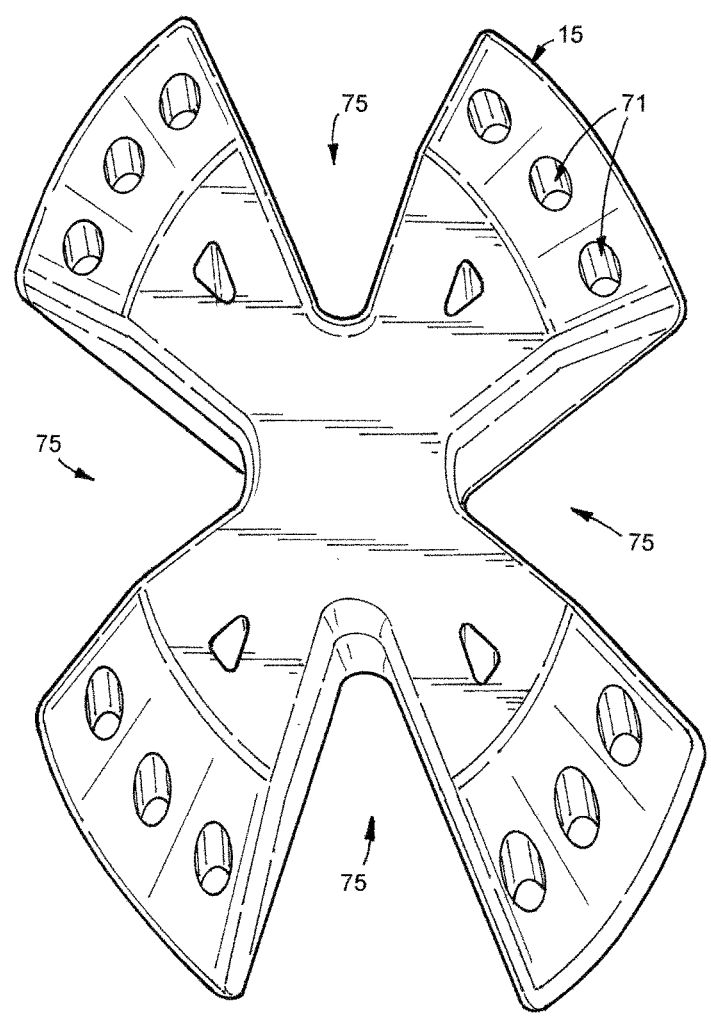
FIGS. 37 and 38 show another alternative head for the novel tethering device shown in FIGS. 1 and 2.
Figure 38:
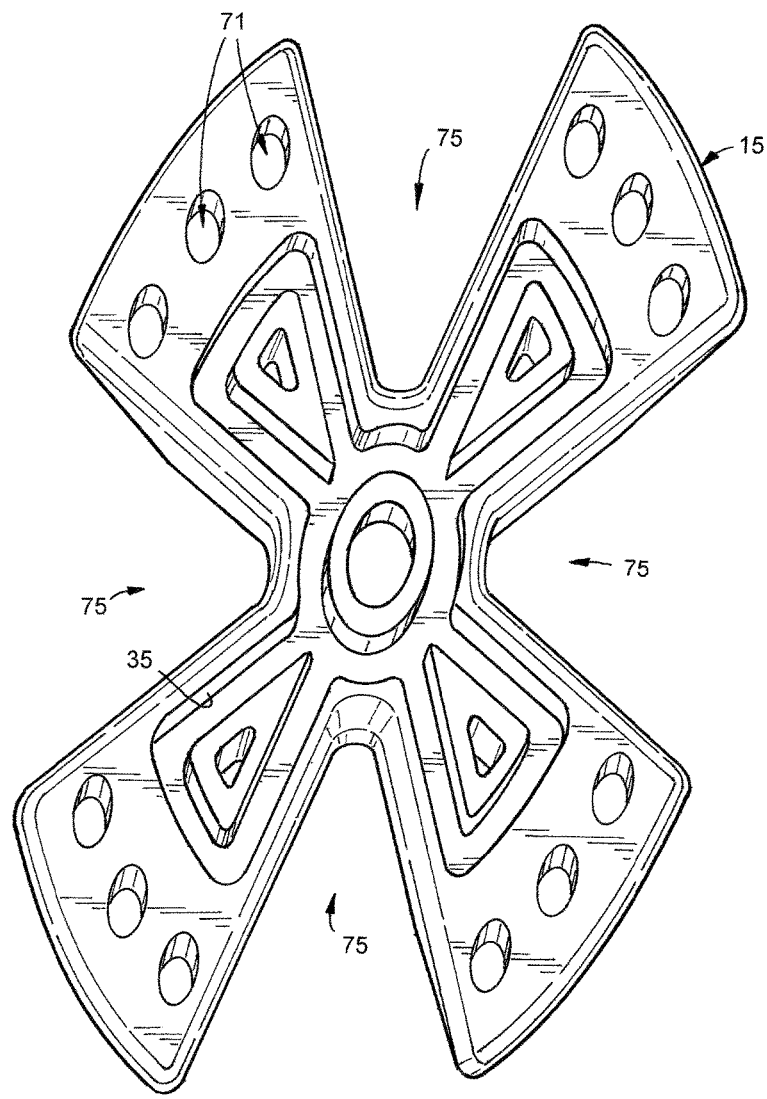

Alternatively, and looking now at FIG. 35-36 (or FIGS. 37 and 38), head 15 can be formed with the material between the lobes removed, e.g., at 75, whereby to further facilitate head folding and to further reduce the risk that head 15 could obstruct an airway in the event of device failure and aspiration. If desired, the lobes can be rounded off so as to reduce device mass and so as to render them even more atraumatic to the tissue.

Figure 39:
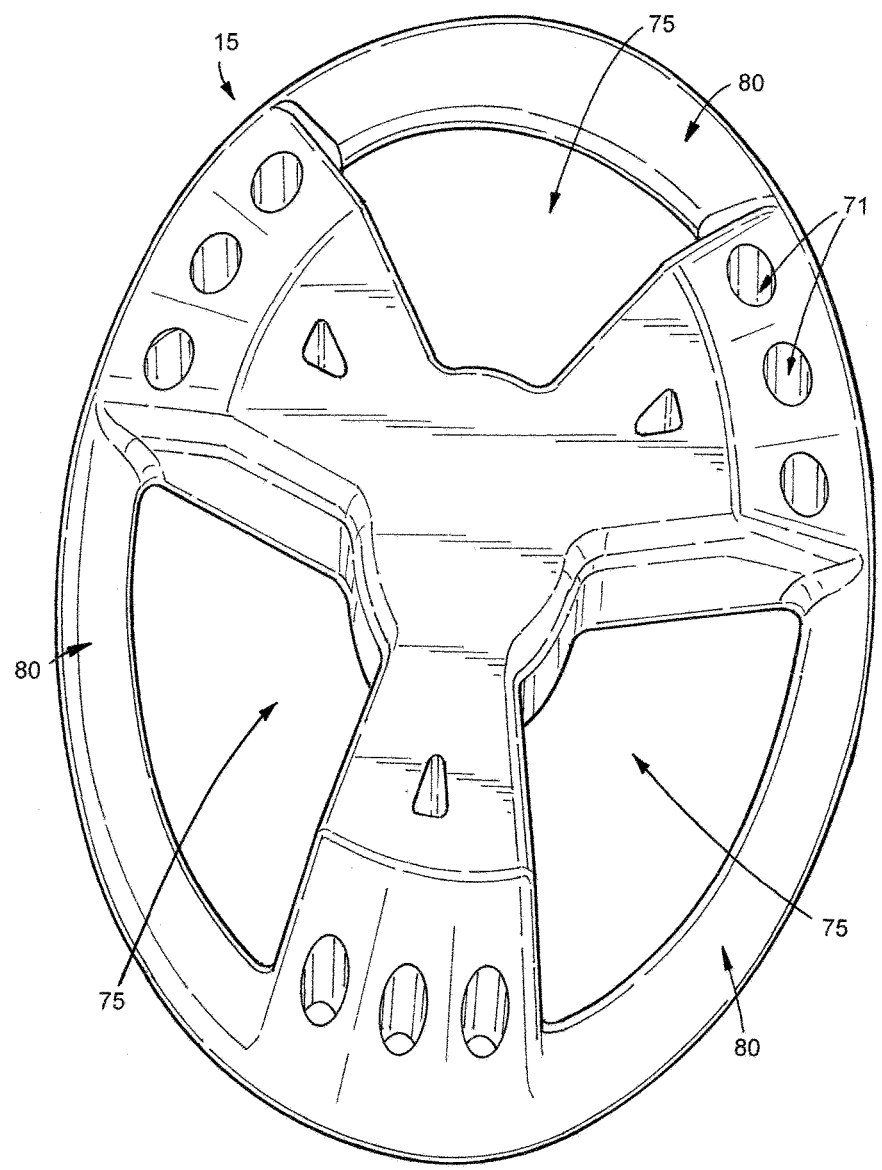
FIG. 39 shows still another alternative head for the novel tethering device shown in FIGS. 1 and 2.
Figure 40:
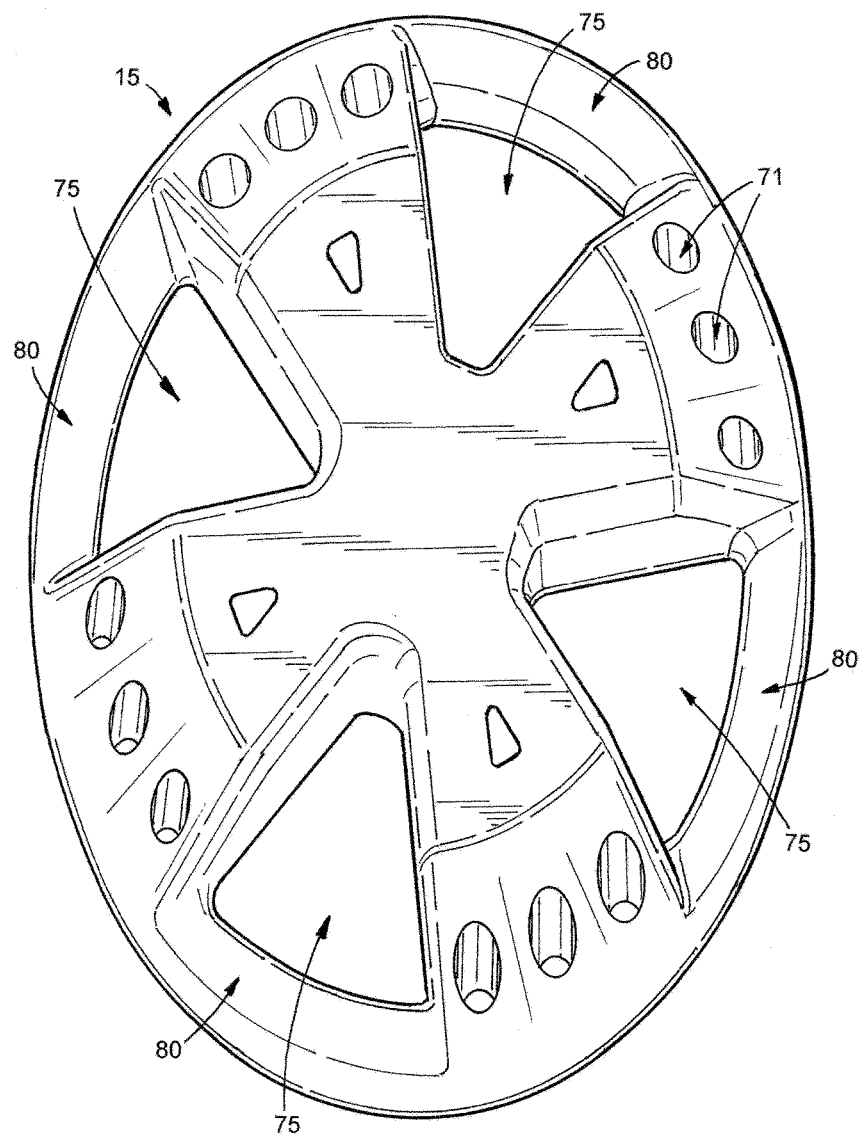
FIG. 40 shows yet another alternative head for the novel tethering device shown in FIGS. 1 and 2.

If desired, and looking now at FIG. 39 (or FIG. 40), a rim 80 of material can extend across the open space 75 which is located between the lobes, at the periphery of the head, so as to provide additional head integrity, and rendering the head even more atraumatic, while still protecting against airway blockage in the event of device failure and aspiration.

In some circumstances it can be desirable to provide visual guidance to assist in proper placement of tethering device 5 within tongue T. Thus, in one preferred form of the invention, tethering device 5 is set within tongue T using X-ray visualization.

Figure 41:
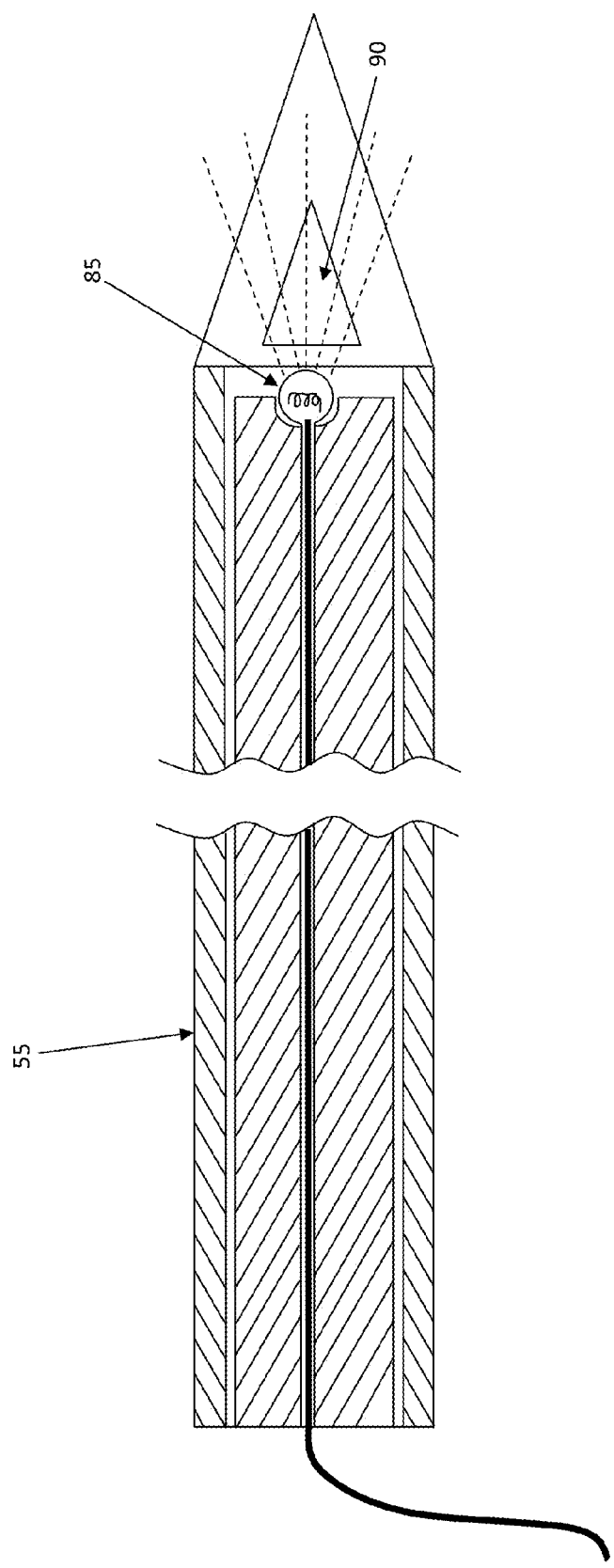
FIGS. 41-43 show various configurations of a lighted corridor trocar which may be used in accordance with the present invention.
Figure 42:
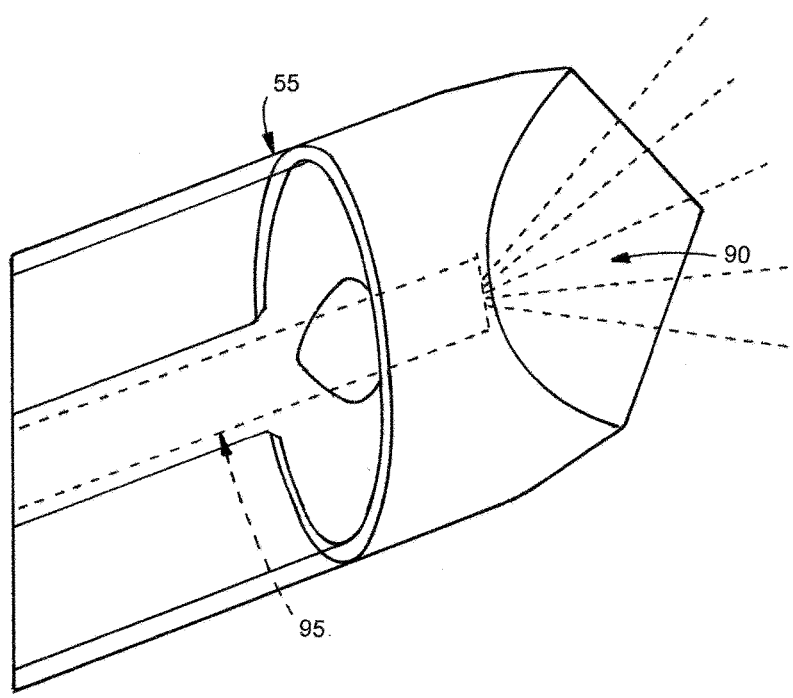
Figure 43:
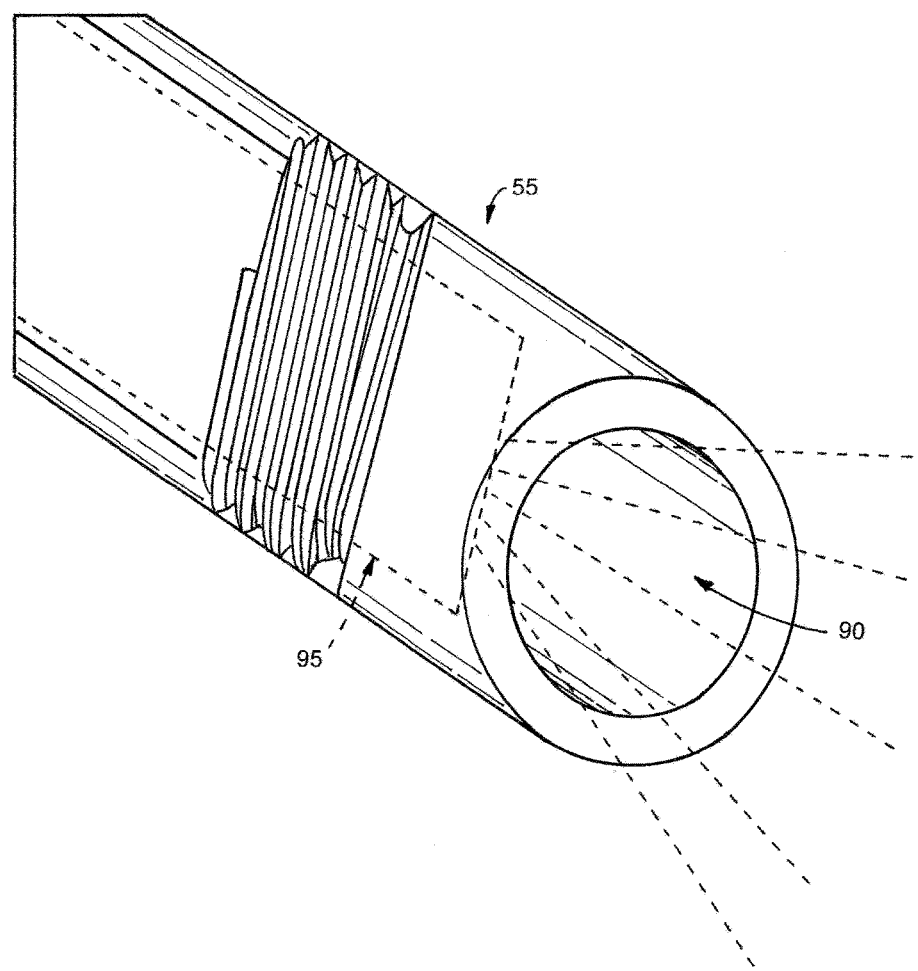

In another preferred form of the invention, proper placement of tethering device 5 is achieved using a light-emitting trocar. More particularly, and looking now at FIG. 41, corridor trocar 55 may include a light source 85 disposed within its distal end, and a window 90 for permitting light from light source 85 to project out the distal end of corridor trocar 55. Alternatively, and looking now at FIGS. 42 and 43), the light source may be disposed at the proximal end of corridor trocar 55 and light from the light source delivered to the distal end of corridor trocar 55 by means of an optical fiber 95 (or a light pipe, etc.). In this form of the invention, light is projected from the distal end of corridor trocar 55 while the corridor trocar (and its associated corridor sheath 50) are advanced through tongue T—as this occurs, a scope is used to observe the back of the tongue and, as the trocar nears the surface of the tissue, the light from corridor trocar 55 is used to gauge proper positioning of corridor trocar 55 (and hence its associated corridor sheath 50), whereby to ensure subsequent proper positioning of tethering device 5 within the tongue and tongue base. It is anticipated that proper placement of head 15 will be important to the effectiveness of device 5.

MODIFICATIONS

While the present invention has been described in terms of certain exemplary preferred embodiments, it will be readily understood and appreciated by those skilled in the art that it is not so limited, and that many additions, deletions and modifications may be made to the preferred embodiments discussed herein without departing from the scope of the invention.

What is claimed is:

1. A method for treating obstructive sleep apnea, the method comprising:
   providing a tethering device comprising:
   an elastic filament having a terminal distal end and a proximal end; and
   a flexible memory head directly mounted to the terminal distal end of the elastic filament and having a proximal side and a distal side, the flexible memory head comprising a disk structure comprising soft, pliable atraumatic material, the flexible memory head comprising a patterned recess formed in the proximal side of the flexible memory head and a like-patterned head stiffener received in the patterned recess;

advancing the tethering device through the tongue of a patient so that the flexible memory head of the tethering device exits a back of the tongue and is disposed against an external surface of the back of the tongue and the elastic filament of the tethering device extends from the flexible memory head and through the tongue; and securing the proximal end of the elastic filament to the mandible of the patient under tension, whereby to restrain rearward movement of the tongue while the patient is sleeping;

wherein the elastic filament extends from the terminal distal end and away from the distal side of the flexible memory head.

2. A method according to claim 1 further comprising the step of mounting the proximal end of the elastic filament to a bone anchor.

3. A method according to claim 2 wherein the proximal end of the elastic filament comprises a plurality of enlargements; and wherein the plurality of enlargements is used to secure the proximal end of the elastic filament to the bone anchor.

4. A method according to claim 3 wherein the bone anchor comprises a mount having a hole and a slot formed therein; and wherein the plurality of enlargements is sized to pass through the hole but is prevented from passing through the slot.

5. A method according to claim 1 wherein the tethering device is advanced through the tongue of the patient using a corridor sheath having a lumen extending therethrough, a corridor trocar, an outer inserter tube having a lumen extending therethrough, and an inner inserter tube having a lumen extending therethrough, wherein the corridor trocar is sized to fit within the lumen of the corridor sheath, the outer inserter tube is sized to fit within the lumen of the corridor sheath, the inner inserter tube is sized to fit within the lumen of the outer inserter tube, and the lumen of the inner inserter tube is sized to receive the elastic filament therethrough.

6. A method according to claim 5 wherein the corridor trocar comprises a light source.

7. A method according to claim 1 wherein the head stiffener comprises a superelastic material.

8. A method according to claim 7 wherein the head stiffener comprises Nitinol.

9. A method according to claim 1 wherein the flexible memory head comprises a multi-lobe structure comprising the soft, pliable atraumatic material.

10. A method according to claim 9 wherein the recess of the flexible memory head comprises a multi-lobe recess and the head stiffener of the flexible memory head comprises a multi-lobe head stiffener.

11. A method according to claim 1 wherein the proximal end of the elastic filament comprises a plurality of enlargements.

12. A method according to claim 11 wherein each enlargement of the plurality of enlargements is frustoconical in configuration.

13. A method according to claim 1 wherein the flexible memory head comprises an elastic filament recess formed in the proximal side of the flexible memory head; and wherein the terminal distal end of the elastic filament is disposed within the elastic filament recess.

14. A method according to claim 13 wherein the patterned recess is separate from and surrounds the elastic filament recess.

15. A method according to claim 1 wherein the elastic filament is secured to the head stiffener.

16. A method according to claim 1 wherein the head stiffener comprises a multi-lobe configuration.

17. A method according to claim 1 wherein the disk structure comprises a plurality of holes for passing air therethrough.

18. A method for treating obstructive sleep apnea, the method comprising:

providing a tethering device comprising:
an elastic filament having a terminal distal end and a proximal end; and
a flexible memory head directly mounted to the terminal distal end of the elastic filament and having a proximal side and a distal side, the flexible memory head comprising a patterned recess formed in the proximal side of the flexible memory head and a like-patterned head stiffener received in the patterned recess;

advancing the tethering device through the tongue of a patient so that the flexible memory head of the tethering device exits a back of the tongue and is disposed against an external surface of the back of the tongue and the elastic filament of the tethering device extends from the flexible memory head and through the tongue; and securing the proximal end of the elastic filament to the mandible of the patient under tension, whereby to restrain rearward movement of the tongue while the patient is sleeping;

wherein the elastic filament extends from the terminal distal end and away from the distal side of the flexible memory head.

19. A method for treating obstructive sleep apnea, the method comprising:

providing a tethering device comprising:
an elastic filament having a terminal distal end and a proximal end; and
a flexible memory head directly mounted to the terminal distal end of the elastic filament and having a proximal side and a distal side, the flexible memory head comprising a disk structure comprising soft, pliable atraumatic material, the flexible memory head comprising a patterned recess formed in the proximal side of the flexible memory head and a like-patterned head stiffener received in the patterned recess, the flexible memory head comprising a multi-lobe configuration, the head stiffener comprising a superelastic material;

advancing the tethering device through the tongue of a patient using a corridor sheath having a lumen extending therethrough so that the flexible memory head of the tethering device exits a back of the tongue and is disposed against an external surface of the back of the tongue and the elastic filament of the tethering device extends from the flexible memory head and through the tongue; and securing the proximal end of the elastic filament to the mandible of the patient under tension, whereby to restrain rearward movement of the tongue while the patient is sleeping;

wherein the tethering device is advanced through the tongue of the patient using the corridor sheath, a corridor trocar, and outer inserter tube having a lumen extending therethrough, and an inner inserter tube having a lumen extending therethrough;

wherein the corridor trocar is sized to fit within the lumen of the corridor sheath, the outer inserter tube is sized to fit within the lumen of the corridor sheath, the inner inserter tube is sized to fit within the lumen of the outer inserter tube, and the lumen of the inner inserter tube is sized to receive the elastic filament therethrough; and wherein the corridor trocar comprises a light source; and wherein the elastic filament extends from the terminal distal end and away from the distal side of the flexible memory head.

* * * * *